United States Patent
Kumar et al.

(10) Patent No.: US 6,958,145 B2
(45) Date of Patent: Oct. 25, 2005

(54) SYNTHESIS OF CYCLIC COMPOUNDS

(75) Inventors: Naresh Kumar, New South Wales (AU); Roger Wayne Read, New South Wales (AU)

(73) Assignee: Unisearch Limited, Sydney (AU)

( * ) Notice: Subject to any disclaimer, the term of this patent is extended or adjusted under 35 U.S.C. 154(b) by 188 days.

(21) Appl. No.: 10/312,155

(22) PCT Filed: Jun. 28, 2001

(86) PCT No.: PCT/AU01/00781

§ 371 (c)(1),
(2), (4) Date: Apr. 10, 2003

(87) PCT Pub. No.: WO02/00639

PCT Pub. Date: Jan. 3, 2002

(65) Prior Publication Data

US 2004/0110966 A1 Jun. 10, 2004

(30) Foreign Application Priority Data

Jun. 28, 2000 (AU) .............................. PQ8419

(51) Int. Cl.$^7$ ..................... A61K 31/365; C07D 307/33
(52) U.S. Cl. ..................... 424/78.09; 549/295; 549/324
(58) Field of Search ....................... 424/78.09; 549/295, 549/324

(56) References Cited

U.S. PATENT DOCUMENTS

| | | | | | |
|---|---|---|---|---|---|
| 4,542,169 | A | * | 9/1985 | Costerton | ................... 523/121 |
| 5,248,221 | A | * | 9/1993 | Gerhart et al. | ............... 405/216 |
| 6,060,046 | A | * | 5/2000 | Steinberg et al. | ........ 424/78.09 |
| 6,475,505 | B1 | * | 11/2002 | Stadler | ....................... 424/411 |
| 6,565,868 | B1 | * | 5/2003 | Howarth et al. | ............ 424/408 |

FOREIGN PATENT DOCUMENTS

| WO | WO 96/01294 | 1/1996 |
|---|---|---|
| WO | WO 99/01514 | 1/1999 |
| WO | WO 99/54323 | 10/1999 |

* cited by examiner

*Primary Examiner*—Deborah C. Lambkin
(74) *Attorney, Agent, or Firm*—Nixon & Vanderhye P.C.

(57) ABSTRACT

A method for the preparation of a compound of formula (II) wherein $R_1$ and $R_2$ are independently H, alkyl, alkoxy, oxoalkyl, alkenyl, aryl or arylalkyl whether unsubstituted or substituted, optionally interrupted by one or more hetero atoms, straight chain or branched chain, hydrophilic, hydrophobic or fluorophilic; $R_3$, $R_4$, $R_5$ and $R_6$ are independently or all hydrogen or halogen; provided that at least two of the $R_3$, $R_4$, $R_5$ and $R_6$ are halogens.

8 Claims, 5 Drawing Sheets

Growth of *Staphylococcus aureus* against compound 63

Growth of *Staphylococcus aureus* against compound 105.

Growth of *Candida albicans* against compound 73

SYNTHESIS OF CYCLIC COMPOUNDS

TECHNICAL FIELD

The present invention relates to novel synthesis methods, to the products of such novel methods, and to uses of these products. In particular, the present invention provides methods for the cyclisation of substituted or unsubstituted halogenated 4-oxo-alkanoic acids (halogenated levulinic acids) and to the products of such a method. The invention has particular application in the synthesis of furanones including fimbrolides (halogenated 5-methylene-2(5H)-furanones) and their synthetic analogues. The invention also relates to novel furnanone compounds and uses thereof.

BACKGROUND ART

Fimbrolides (halogenated 5-methylene-2(5H)-furanones) possess a wide range of important biological properties including antifungal and antimicrobial properties (see WO 96/29392 and WO 99/53915, the disclosures of which are incorporated herein by cross-reference). These metabolites can be isolated from red marine algae *Delisea fimbriata*, *Delisea elegans* and *Delisea pulchra*.

In spite of recently discovered biological significance of fimbrolides, there is not at present a general method suitable for the large-scale synthesis of these metabolites. The few reported syntheses of these metabolites utilise either the sulfuric acid-catalysed cyclisation of brominated levulinic acid at elevated temperatures (Tetrahedron 1997, 53: 15813–15826) or use (E)-β-bromo-β-lithioacrylate (J. Org. Chem. 1985, 50, 2195–2198) or allenes (J. Org. Chem. 1995, 60, 1814–1822) as starting materials.

Known acids used in the cyclisation reaction include 100% or 98% sulfuric acid which causes a high degree of charring during the reaction thus producing large quantities of intractable materials. Furthermore copious amounts of water are required to quench these reactions, a process that generates a large quantity of aqueous acidic waste.

These reactions are non-selective, extremely difficult to control and lead to mixtures of different products due to scrambling of bromines atoms under these conditions. Exhaustive chromatography is required to separate the reaction products and this results in low yields of desired 4-bromo-5-(bromomethylene)-, 5-(dibromomethylene)-, 4-bromo-5-(dibromomethylene)-2(5H)-furanones. The chromatography required is tedious and often impractical for large scale reactions.

The compounds 3-alkyl-4-bromo-5-(bromomethylene)- and 3-alkyl-5-(dibromomethylene)-2(5H)furanones are key intermediates in the synthesis of highly of active side chain functionalised furanones (see WO 99/54323, the disclosure of which is incorporated herein by cross-reference). Accordingly, there is a need for more efficient and reliable syntheses of parent furanones.

We have found conditions that, surprisingly, enable the cyclisation of halogenated 4-oxoalkanoic acids under mild conditions. We have found this discovery to be particularly useful in cyclising brominated 4-oxopentanoic acids under mild conditions to afford high yields of brominated 2(5H) furanones or tetrahydro-2(5H)-furanones under mild conditions. Furthermore tetrahydrofuranones generated under these conditions can be dehydrobrominated to yield a range of 5-(methylene)-, 5-(bromomethylene)-, 5-(dibromomethylene)- or 4-bromo-5-(bromomethylene)-2 (5H)-furanones. These furanones can be further functionalised to yield novel analogues of *Delisea* metabolites.

DISCLOSURE OF INVENTION

In a first aspect, the present invention provides a method for the preparation of a compound of formula II

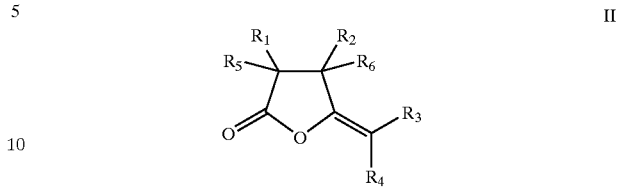

wherein $R_1$ and $R_2$ are independently H, alkyl, alkoxy, oxoalkyl, alkenyl, aryl or arylalkyl whether unsubstituted or substituted, optionally interrupted by one or more hetero atoms, straight chain or branched chain, hydrophilic, hydrophobic or fluorophilic;
$R_3$, $R_4$, $R_5$ and $R_6$ are independently or all hydrogen or halogen; and provided that at least two of the $R_3$, $R_4$, $R_5$ and $R_6$ are halogens;
the method comprising cyclising a compound of formula I

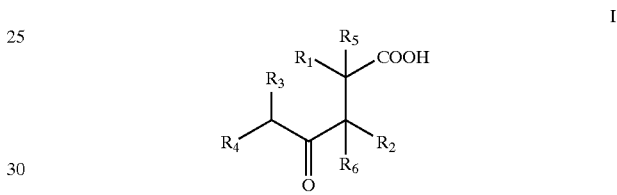

wherein $R_1$, $R_2$, $R_3$, $R_4$, $R_5$ and $R_6$ are as defined above, wherein the cyclisation is carried out in the presence of a mild acid catalyst or a dehydrating agent or a mixture thereof, optionally in the presence of solvent.

In formula II, a particular geometry is not to be taken as specified. For example, the formula covers both Z- and E-isomers.

The starting 4-oxoalkanoic acid of formula I and the tetrahydrofuranone of formula II preferably have the following substituents wherein:
$R_1$ and $R_2$ are independently H, alkyl, alkoxy, oxoalkyl, alkenyl, aryl or arylalkyl whether unsubstituted or substituted, optionally interrupted by one or more hetero atoms, straight chain or branched chain, hydrophilic, hydrophobic or fluorophilic;
$R_3$, $R_4$, $R_5$ and $R_6$ are independently or all hydrogen or halogen; and provided that at least two of the $R_3$, $R_4$, $R_5$ and $R_6$ are halogens (F, Cl, Br, I);

More preferably, the starting levulinic acid of formula I and the tetrahydrofuranone of formula II have the following substituents wherein:
$R_1$ and $R_2$ are independently H, alkyl, oxoalkyl, alkenyl, aryl or arylalkyl whether unsubstituted or substituted, optionally interrupted by one or more hetero atoms, straight chain or branched chain, hydrophilic, hydrophobic or fluorophilic;
$R_3$, $R_4$, $R_5$ and $R_6$ are independently or all hydrogen or halogens; and provided that at least two of the $R_3$, $R_4$, $R_5$ and $R_6$ are halogens (F, Br, I);

Most preferably, the staring levulinic acid of formula I and the tetrahydrofuranone of formula II have the following substituents wherein:
$R_1$ and $R_2$ are independently H, alkyl, aryl or arylalkyl whether unsubstituted or substituted, optionally interrupted by one or more hetero atoms, straight chain or branched chain, hydrophilic, hydrophobic or fluorophilic;

$R_3$, $R_4$, $R_5$ and $R_6$ are independently or all hydrogen or halogen; and provided that at least two of $R_3$, $R_4$, $R_5$ and $R_6$ are halogens (F, Br, I);

Most preferably, at least one of $R_5$ and $R_6$ is Br.

The method of the present invention has particular application in the cyclisation of brominated 4-oxopentanoic acid compounds of formula I wherein at least two of $R_3$, $R_4$, $R_5$ and $R_6$ are halogens. Preferably, the compound of formula II produced by the method of the present invention is selected from halogenated 2-tetrahydrofuranones.

The term "alkyl" is taken to mean both straight chain alkyl groups such as methyl, ethyl, propyl, isopropyl, butyl, isobutyl, sec-butyl, tertiary butyl, and the like. Preferably the alkyl group is a lower alkyl of 1 to 6 carbon atoms. The alkyl group may optionally be substituted by one or more groups selected from alkyl, cycloalkyl, alkenyl, alkynyl, halo, haloalkyl, haloalkynyl, hydroxy, alkoxy, alkenyloxy, haloalkoxy, haloalkenyloxy, nitro, amino, nitroalkyl, nitroalkynyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocyclyl, heterocycloxy, heterocyclamino, haloheterocyclyl, alkylsulfenyl, alkylcarbonyloxy, alkylthio, acylthio, phosphorus-containing groups such as phosphono and phosphinyl.

The term "alkoxy" denotes straight chain or branched alkyloxy, preferably $C_{1-10}$ alkoxy. Examples include methoxy, ethoxy, n-propoxy, isopropoxy and the different butoxy isomers.

The term "alkenyl" denotes groups formed from straight chain, branched or mono- or polycyclic alkenes and polyene. Substituents include mono- or poly-unsaturated alkyl or cycloalkyl groups as previously defined, preferably $C_{2-10}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, or 1,3,5,7-cyclooctatetraenyl.

The term "halogen" denotes fluorine, chlorine, bromine or iodine, preferably bromine or fluorine.

The term "heteroatoms" denotes O, N or S.

The term "acyl" used either alone or in compound words such as "acyloxy", "acylthio", "acylamino" or diacylamino" denotes an aliphatic acyl group and an acyl group containing a heterocyclic ring which is referred to as heterocyclic acyl, preferably a $C_{1-10}$ alkanoyl. Examples of acyl include carbamoyl; straight chain or branched alkanoyl, such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl; alkoxycarbonyl, such as methoxycarbonyl, ethoxycarbonyl, t-butoxycarbonyl, t-pentyloxycarbonyl or heptyloxycarbonyl; cycloalkanecarbonyl such as cyclopropanecarbonyl cyclobutanecarbonyl, cyclopentanecarbonyl or cyclohexanecarbonyl; alkanesulfonyl, such as methanesulfonyl or ethanesulfonyl; alkoxysulfonyl, such as methoxysulfonyl or ethoxysulfonyl; heterocycloalkanecarbonyl; heterocyclyoalkanoyl, such as pyrrolidinylacetyl, pyrrolidinylpropanoyl, pyrrolidinylbutanoyl, pyrrolidinylpentanoyl, pyrrolidinylhexanoyl or thiazolidinylacetyl; heterocyclylalkenoyl, such as heterocyclylpropenoyl, heterocyclylbutenoyl, heterocyclylpentenoyl or heterocyclylhexenoyl; or heterocyclylglyoxyloyl, such as, thiazolidinylglyoxyloyl or pyrrolidinylglyoxyloyl.

The term "fluorophilic" is used to indicate the highly attractive interactions between certain groups, such as highly fluorinated alkyl groups of C4–C10 chain length, have for perfluoroalkanes and perfluoroalkane polymers.

The mild acid catalysts may be selected from catalysts that are insoluble in the reaction medium or catalysts that are soluble in the reaction medium. Examples of insoluble acid catalysts include polyphosphoric acid, Eaton's reagent, acidic resins and polymers, Lewis acids, acidic metal salts.

Examples of soluble acid catalysts include chlorosulfonic acid, phosphoric acid, p-toluenesulfonic acid, trifluoromethanesulfonic acid, methanesulfonic acid, acetic acid, bromine, phosphorus tribromide and hydrobromic acid.

Examples of suitable dehydrating agents include phosphorus pentoxide, silica gel, molecular sieves, alumina, phosphorus oxychloride, acetic anhydride, N,N'-dicyclohexyl-carbodiimide (DCC), trifuoroacetic anhydride, trifluorosulfonic acid anhydride (triflic anhydride).

Preferably cyclisation is carried out using phosphorus pentoxide or polyphosphoric acid by itself or mixed with a mineral acid. More preferably cyclisation is carried out using phosphorus pentoxide.

The cyclisation may be performed with a mild acid or a dehydrating agent in the presence or absence of a solvent. The solvent may be any suitable solvent. Preferable solvents in the present invention include alkyl acetates, aromatic hydrocarbons, chlorinated alkanes, tetrahydrofuran, diethyl ether, dioxane and C1–C3 acids. More preferably, the solvents are aromatic hydrocarbons and chlorinated alkanes. Most preferably, the solvent is dichloromethane, as well as dichloroethane and trichloroethane.

The reaction is preferably carried out at mild temperatures. Preferably the cyclisation reaction is performed at a temperature in the range of from about 20–150° C. Where a solvent is present, the cyclisation may be performed at reflux temperature of the solvent, for example, at the reflux temperature of dichloromethane.

The reaction time may range from about 2 hours to 12 hours or more and is typically about 2 hours or more. It will be appreciated that reaction conditions may be varied depending on the individual nature of the substrate and the desired rate of the reaction.

In the case of halogenated 4-oxoalkanoic acids, whilst the parent levulinic acid is commercially available, the corresponding alkyl substituted 4-oxoalkanoic acids can be prepared from the condensation of ethyl acetoacetate with alkyl haloalkanoates followed by hydrolysis and decarboxylation of the keto ester (Tetrahedron, 1997, 53, 15813). Di-, tribromolevulinic acids are readily obtained by the bromination of the corresponding levulinic acids, for example with bromine and catalytic hydrobromic acid.

Alternatively the brominated 4-oxoalkanoic acid derivatives can be conveniently obtained by the addition of bromine or hydrogen bromide to the corresponding 4-oxo-3-alkyl-2-pentenoic acids.

The present invention extends to these brominated intermediates including those novel compounds of formula I.

Representative examples of 3-alkyl-2,3-dibromo-4-oxoalkanoic acids (1a-i) prepared for use in this invention are listed below.

1a 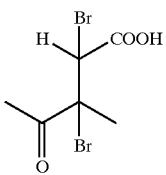

1b 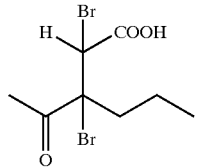

1c 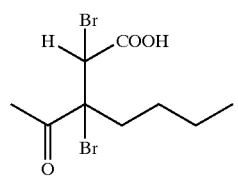

1d 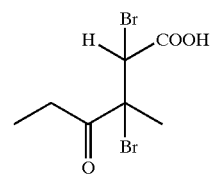

1e 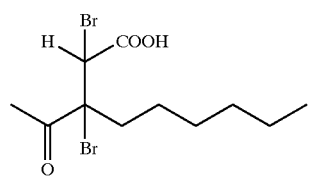

1f 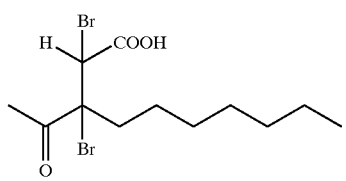

1g 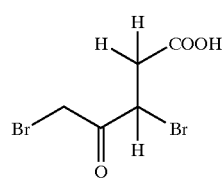

1h 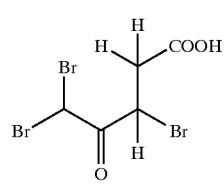

-continued

1i 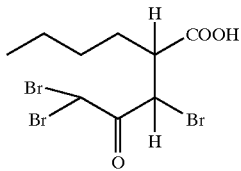

The present inventors have found that with a judicious choice of acid catalysts and solvents, the brominated levulinic acids could be cyclised with few side products and in high yields to the corresponding tetrahydro-2(5H)-furanones. In particular the use of phosphorus pentoxide in dichloromethane provided very efficient cyclisation of the levulinic acids to tetrahydro-2(5H)-furanones.

The surprising results obtained by the present inventors are in sharp contrast to those reported in the literature for attempted cyclisation of brominated levulinic acid. It has been reported that when 5-bromolevulinic acid was treated with relatively mild dehydrating agents (trifluoroacetic acid or dicyclohexylcarbodiimide) the major product of the cyclisation reaction was a cyclic alkyl bromide (J. Am. Chem. Soc., 1981, 103, 5459).

No further reaction of the tetrahydrofuranone was observed even if the reaction was continued for a longer period of time. This reaction appears to be quite general and was repeated on a hundred gram scale.

Representative examples of tetrahydrofuranones (2a-i) that can be synthesised by this procedure are listed below.

2a 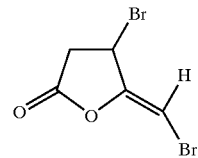

2b 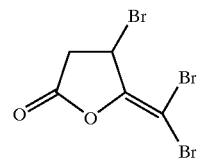

2c 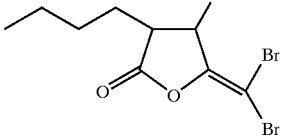

2d 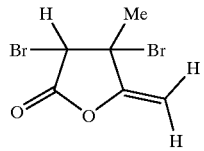

2e 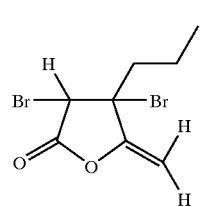

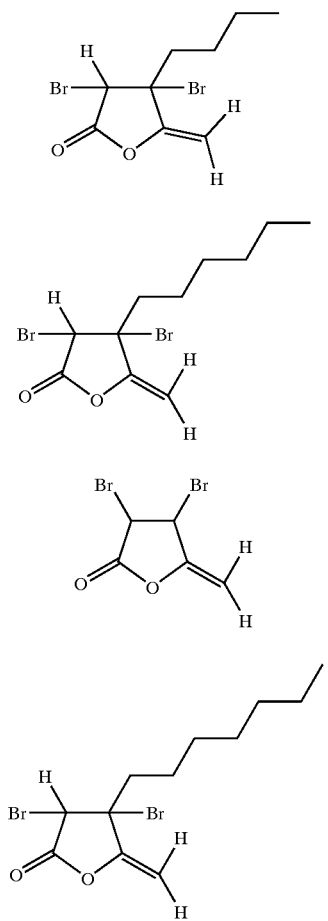

In a second aspect, the present invention consists in a tetrahydro-2(5H)-furanone derivative of formula II, wherein $R_1$ and $R_2$ are independently H, alkyl, alkoxy, oxoalkyl, alkenyl, aryl or arylalkyl whether unsubstituted or substituted, optionally interrupted by one or more hetero atoms, straight chain or branched chain, hydrophilic, hydrophobic or fluorophilic;

$R_3$, $R_4$, $R_5$ and $R_6$ are independently or all hydrogen or halogen; and provided that at least two of the $R_3$, $R_4$, $R_5$ and $R_6$ are halogens;

with the proviso $R_1=R_2=H$, $R_3=R_4=Cl$, $R_5=R_6=Br$;

$R_1,=R_2=R_5,=R_6=H$, $R_3$, $R_4=Cl$.

The inventors have found the brominated tetrahydrofuranones of formula II can be dehydrobrominated to yield a range of 5-(methylene)-2(5H)-furanones, 5-(dibromomethylene)-2(5H)-furanones or 4-bromo-5(bromomethylene)-2(5H)-furanones.

We believe that the 2(5H)-furanones prepared in accordance with the present invention are novel compounds.

In a third aspect, the present invention provides a method for the dehydrohalogenation of a compound of formula II above, provided that at least two of the $R_3$, $R_4$, $R_5$ and $R_6$ are halogens; to prepare a compound of formula IIIa or IIIb;

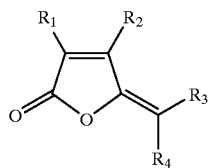

wherein $R_2$ is an alkyl, alkoxy, oxoalkyl, alkenyl, aryl or arylalkyl whether unsubstituted or substituted, straight chain or branched chain, hydrophobic, hydrophilic or fluorophilic;
$R_4$ is a halogen (X=F, Cl, Br or I);
$R_1$ and $R_3$ are independently or both hydrogen or halogen;

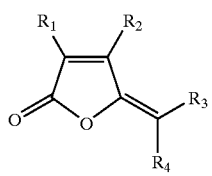

wherein $R_2$ is an alkyl, alkoxy, oxoalkyl, alkenyl, aryl or arylalkyl whether unsubstituted or substituted, straight chain or branched chain, hydrophobic, hydrophilic or fluorophilic;
$R_3$ and $R_4$ are hydrogen and $R_1$ is a halogen;
the method comprising contacting a compound of formula II with a base.

The compound of formula II used in the second aspect of the invention may be a compound of formula II produced by the method of the first aspect of the invention, although compounds of formula II produced by other methods may be used.

Dehydrobromination of the tetrahydrofuranones to 5-(methylene)-, 5-(bromomethylene)- and 5-(dibromomethylene)-2(5H)-fulranones may be accomplished by treatment of the tetrahydrofuranones with a base e.g. 1,4-diazabicyclo[2.2.2]octane (DABCO), 4-(dimethylamino)pyridine (DMAP), 1,8-diazabicyclo[5.4.0]undec-7-ene (DBU), triethylamine, sodium or potassium carbonate, sodium or potassium acetate and N,N'-diisopropylethyl amine (Hunig's base).

Representative examples of furanones (3a–n) that can be synthesised by this procedure are listed below.

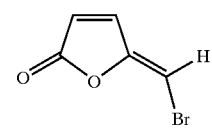

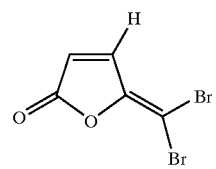

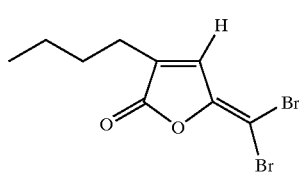

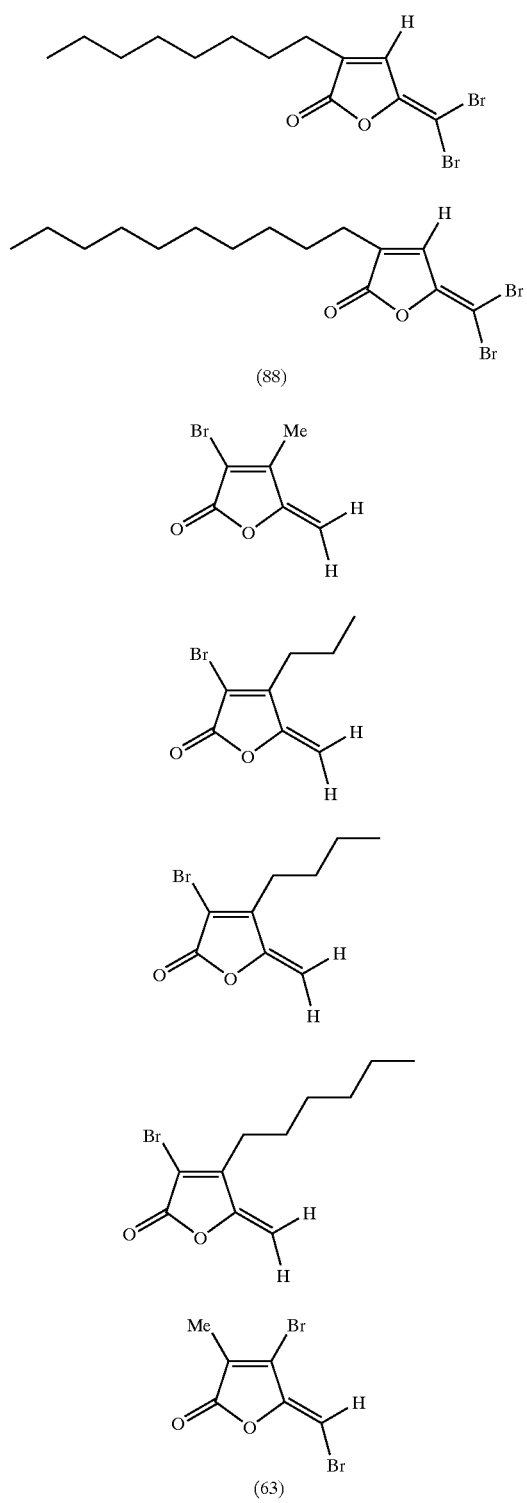
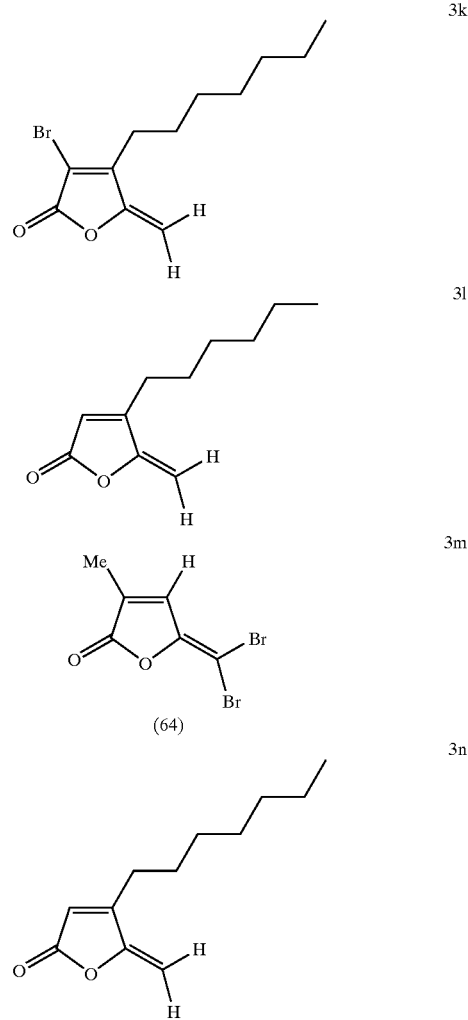

In a fourth aspect, the present invention consists in a 2(5H)-furanone derivative having formula IIIa or IIIb;

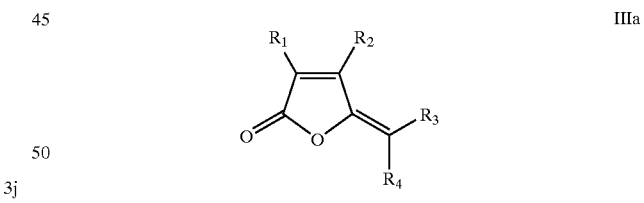

wherein $R_2$ is an alkyl, alkoxy, oxoalkyl, alkenyl, aryl or arylalkyl whether unsubstituted or substituted, straight chain or branched chain, hydrophobic, hydrophilic or fluorophilic;
$R_4$ is a halogen (X=F, Cl, Br or I);
$R_1$ and $R_3$ are independently or both hydrogen or halogen;
with the proviso that $R_1$=H, $R_2$=Me or Ph, $R_3$=I, $R_4$=H; and $R_1$=H, $R_2$=OMe, $R_3$=Cl, $R_4$=Cl,

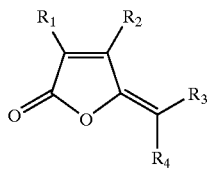

IIIb wherein $R_2$ is an alkyl, alkoxy, oxoalkyl, alkenyl, aryl or arylalkyl whether unsubstituted or substituted, straight chain or branched chain, hydrophobic, hydrophilic or fluorophilic; and $R_3$ and $R_4$ are hydrogen and $R_1$ is a halogen.

In a fifth aspect, the present invention provides a method for the halogenation of a compound of formula II, IIIa or IIIb above to prepare a compound of formula IV

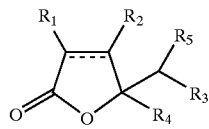

IV wherein $R_2$ is independently H, halogen, alkyl, alkoxy, oxoalkyl alkenyl, aryl or arylalkyl whether unsubstituted or substituted, straight chain or branched chain, hydrophilic or fluorophilic;

$R_4$ and $R_5$ are halogen (X=F, Cl, Br or I); $R_4$ can also be OH or alkoxy;

$R_1$ and $R_3$ are independently or both hydrogen or halogen; and

"====" is a single bond or double bond, the method comprising contacting a compound of formula III with a halogenating agent in the absence of solvent or in the presence of an unreactive or reactive solvent or reagent.

Halogenation of the 2(5H)-furanones of formula (III) to 5-halo-5-halomethyl- or 5-halo-5-dihalomethyl-2(5H)-furanones of formula IV) may achieved by treatment of the 2(5H)-furanone with an halogenating agent e.g. bromine, chlorine, iodine, N-bromosuccinimide, N-chlorosuccinimde, iodine monochloride, phenyltrimethylammonium bromide perbromide, pyridinium tribromide and cupric bromide.

Unreactive solvents and reagents are non-nucleophilic organic solvents or ionic liquids, including dichloromethane, chloroform, toluene, diethyl ether, N,N-dimethylformamide, N-methylpyrrolidinone, butylmethylimidazolium tetrafluoroborate.

Reactive solvents and reagents are nuceophilic organic or inorganic substances such as water, methanol, acetic acid, lithium chloride, benzylamine and silver nitrate.

Representative examples of furanones (4a–p) that can be synthesised by this procedure are listed below.

4a

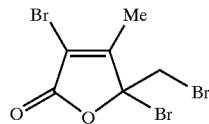

4b

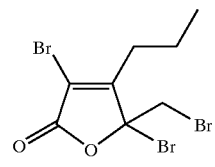

4c

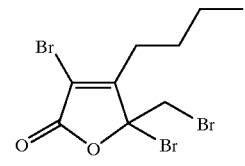

4d

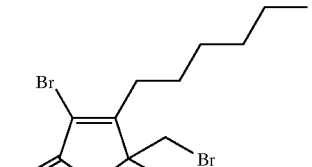

4e

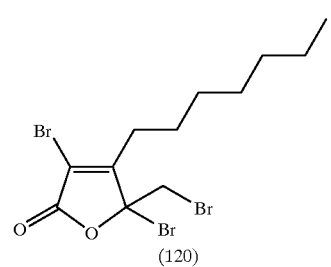

(120)

4f

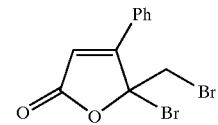

4g

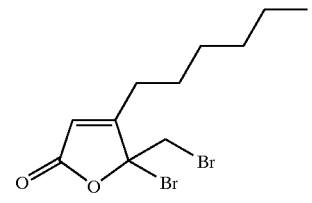

4h

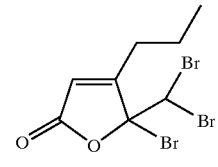

4i

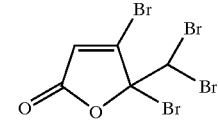

4j

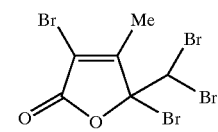

-continued

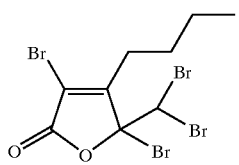
4k

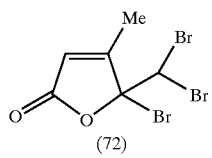
(72)
4l

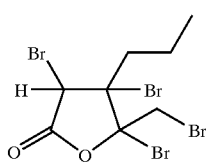
4m

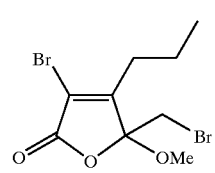
4n

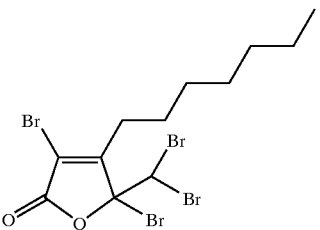
4o

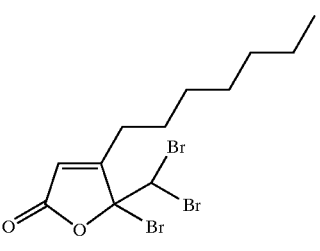
4p

In a sixth aspect, the present invention consists in a 2(5H)-furanone of formula IV,

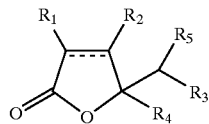
IV wherein $R_2$ is independently alkyl, alkoxy, oxoalkyl, alkenyl, aryl or arylalkyl whether unsubstituted or substituted, straight chain or branched chain, hydrophilic or fluorophilic;

$R_4$ and $R_5$ are halogen (X=F, Cl, Br or I); $R_4$ can also be OH or alkoxy;

$R_1$ and $R_3$ are independently or both hydrogen or halogen; and

"====" is a single bond or double bond.

In yet a seventh aspect, the present invention provides a method for the dehydrohalogenation of a compound of formula IV above, to prepare a compound of formula V

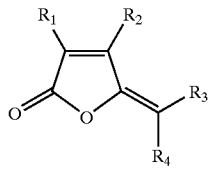
V wherein $R_2$ is a H, alkyl, alkoxy, oxoalkyl, alkenyl, aryl or arylalkyl whether unsubstituted or substituted, straight chain or branched chain, hydrophobic, hydrophilic or fluorophilic;

$R_4$ is a halogen (X=F, Cl, Br or I);

$R_1$ and $R_3$ are independently or both hydrogen or halogen;

the method comprising contacting a compound of formula IV with a base.

The compound of formula IV used in the seventh aspect of the invention may be a compound of formula IV produced by the method of the fifth aspect of the invention, although compounds of formula IV produced by other methods may be used.

Dehydrohalogenation of the to 5-halo-5-halomethyl- or 5-halo-5-dihalomethyl-2(5H)-furanones of formula (IV) may be accomplished by treatment of the furanones with a base e.g. 1,4-diazabicyclo[2.2.2]octane (DABCO), 4-(dimethylamino)pyridine (DMAP), 1,8-diazabicyclo [5.4.0]undec-7-ene (DBU), triethylamine, sodium or potassium carbonate, sodium or potassium acetate and N,N'-diisopropylethyl amine (Hunig's base).

Surprisingly the present inventors have found that the dehydrohalogenation of compounds of formula (IV) where $R_1$ is a halogen cannot be achieved satisfactorily by the use of the above mentioned reagents. Pleasingly the present inventors have found that dehydrohalogenation of these compounds can be achieved successfully by the use of N,N-diisopropylethyl amine.

Representative examples of furanones (5a–m) that can be synthesised by this procedure are listed below.

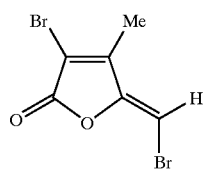
5a

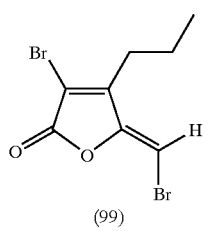
(99)
5b

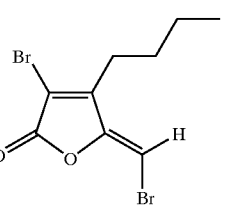
5c

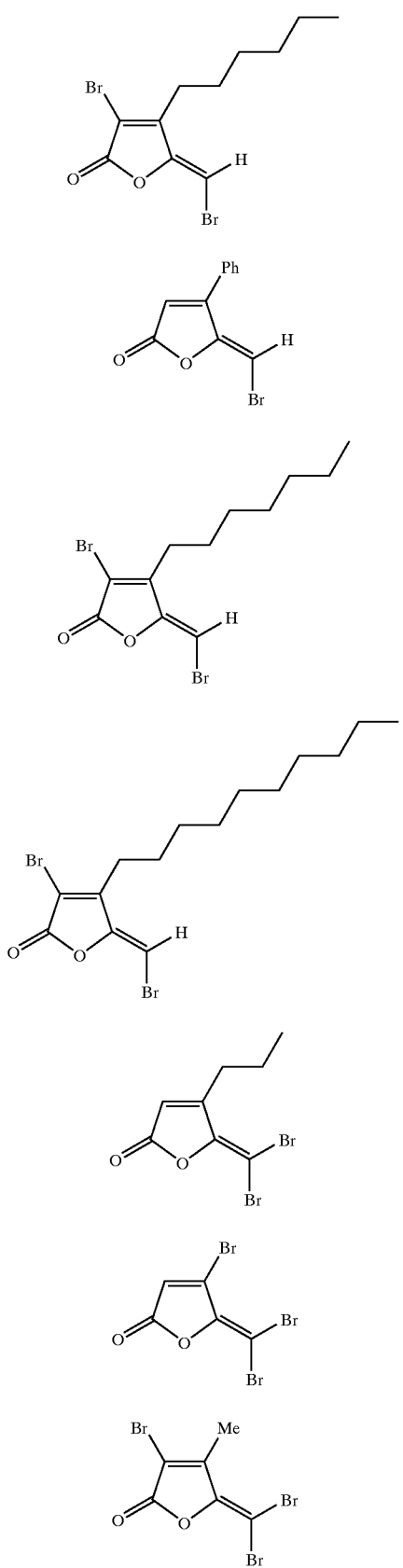

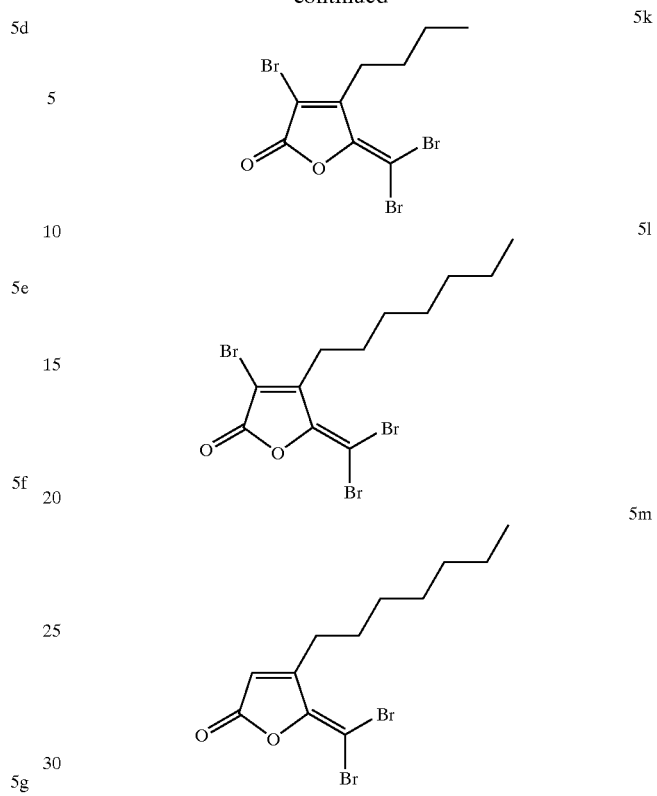

In an eighth aspect, the present invention consists in a 2(5H)-furanone of derivative of formula V, wherein $R_2$ is an alkyl, alkoxy, oxoalcyl, alkenyl, aryl or arylalkyl whether unsubstituted or substituted, straight chain or branched chain, hydrophobic, hydrophilic or fluorophilic; $R_4$ is a halogen (X=F, Cl, Br or I); $R_1$ and $R_3$ are independently or both hydrogen or halogen; with the proviso that $R_1$=H, $R_2$=Me or Ph, $R_3$=I, $R_4$=H; and $R_1$=H, $R_2$=OMe, $R_3$=Cl, $R_4$=Cl.

Furthermore the present inventors have also found that halogenated 4-oxoalkanoic acid substrates of formula (I) where $R_5$ and $R_6$ are halogens, when treated with sulfuric acid undergo lactonisation with concomitant dehalogenation rather than oxidation as reported in the literature. The halogen produced in this reaction is consumed in situ to produce compounds of formula (VI).

For example when 3-alkyl-2,3-dibromo-4-oxopentanoic acid was treated with sulfuric acid it underwent clean cyclisation with concomitant debromination and utilisation of the liberated bromine through a bromination-dehydrobromination sequence to yield 4-alkyl-5-(bromomethylene)-2(5H)-furanone in good yields. Similarly 2,3,5-tribromo-4-oxopentanoic acid and 2,3-dibromo-4-oxopentanoic acid gave 4-bromo-5-(bromomethylene)-2(5H)-furanone in high yields.

Furthermore compounds of formula (VI) can also be prepared by the treatment of the starting 3-alkyl-4-oxo-2-pentenoic acids with sulfric acid followed by the addition of bromine.

Accordingly, in a ninth aspect the present invention provides a method of concomitant cyclisation and dehalogenation of compounds of formula I as defined above to form a compound of formula (VI), the method comprising contacting the compound with sulfuric acid or other strong acid.

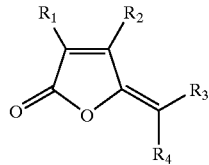

VI wherein $R_2$ is a H, halogen, alkyl, alkoxy, oxoalxyl, alkenyl, aryl or arylalkyl whether unsubstituted or substituted, straight chain or branched chain, hydrophobic, hydrophilic or fluorophilic;

$R_4$ is a halogen (X=F, Cl, Br or I);

$R_1$ is hydrogen; and $R_3$ is a hydrogen or halogen;

The sulfuric acid type reagent may be, for example, concentrated sulfuric acid, oleum, chlorosulfonic acid, or a mixture of sulfuric acid with one or more other like agents.

Examples of compounds of formula I that may be used in the method of the seventh aspect include 3-alkyl-2,3-dibromo-4-oxopentanoic acid, 2,3,5-tribromo-4-oxopentanoic acid, 2,3-dibromo-4-oxopentanoic acid, 2,5-dibromo-4-oxopentanoic acid, 2,3,5,5-tetrabromo-4-oxopentanoic acid, 2,3,3-tribromo-4-oxopentanoic acid and 2,3,3,5-tetrabromo-4-oxopentanoic acid.

Representative examples of furanones (6a–g) that can be synthesised by this procedure are listed below.

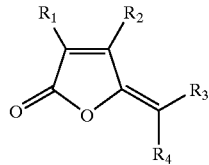
(73)

6a

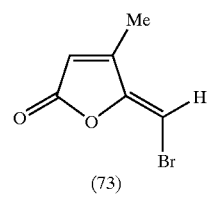
(103)

6b

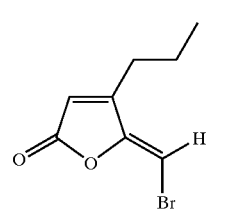

6c

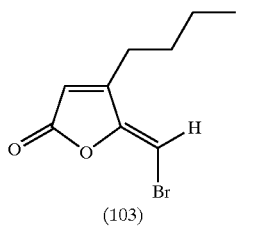

6d

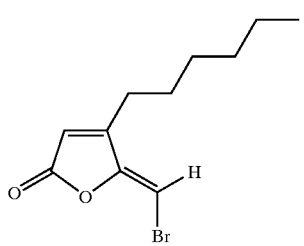

6e

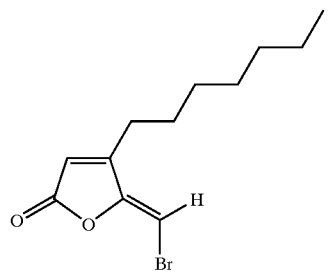

6f

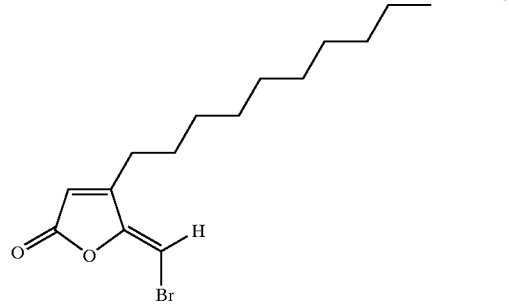

6g

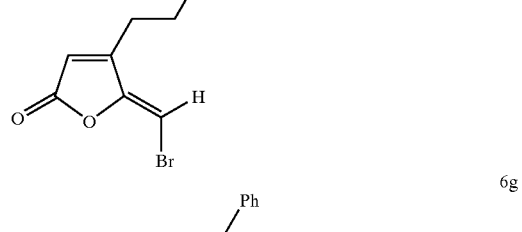

In a tenth aspect, the present invention consists in a 2(5H)-furanone of derivative of formula VI, wherein $R_2$ is an alkyl, alkoxy, oxoalkyl, alkenyl, aryl or arylalkyl whether unsubstituted or substituted, straight chain or branched chain, hydrophobic, hydrophilic or fluorophilic;

$R_4$ is a halogen (X=F, Cl, Br or I);

$R_1$ is hydrogen; and $R_3$ is a hydrogen or halogen;

with the proviso that $R_1$=H, $R_2$=Me or Ph, $R_3$=I, $R_4$=H; and $R_1$=H, $R_2$=OMe, $R_3$=Cl, $R_4$=Cl.

In an eleventh aspect the present invention consists in a fimbrolide derivative, having a formula (VII), wherein $R_2$ is a H, alkyl, alkoxy, polyethyleneglycyl, oxoalkyl, alkenyl, aryl or arylalkyl whether unsubstituted or substituted, straight chain or branched chain, hydrophobic, hydrophilic or fluorophilic;

$R_4$ is a hydrogen, halogen (X=F, Cl, Br or I);

$R_1$ and $R_3$ are independently or both hydrogen or halogen;

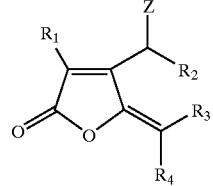

VII

Z is independently selected from the group $R_2$, halogen, $OC(O)R_2$, =O, amine azide, thiol, $R_2$, mercaptoaryl, arylalkoxy, mercaptoarylalkyl, $SC(O)R_2$, $OS(O)_2R_2$, $NHC(O)R_2$, =$NR_2$ or $NHR_2$;

prepared by functionalizing a fimbrolide of formula (VIII) wherein, $R_1$, $R_2$, $R_3$ and $R_4$ are as defined above, with reagent according to our complete specification. (see WO 99/54323, the disclosures of which are incorporated herein by cross-reference).

Reagents including halogenating and oxidising agents (N-halosuccinimide, lead tetraacetate, selenium dioxide, Jones reagent), nucleophiles including (organic metal carboxylates, organic alcohols, dimethyl sulfoxide and organonitriles) and electrophiles including (organic acids, isocyanates, carboxylic or sulfonic acid halides and diethylaminosulfur trifluoride).

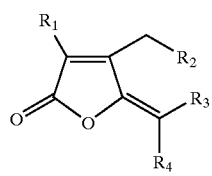

VIII

In a twelfth aspect the present invention provides an oligomer or polymer formed by oligomerising or polymerising a compound of formula III–VII, described in the in the present invention directly or with one or more monomers.

The one or more other monomer may be any suitable polymerisable copolymer e.g. acrylate ester such as alkyl hydroxyalkyl, aminoalkyl, or substituted aryl acrylates or methacrylates, crotonates, substituted or unsubstituted acrylonitriles, vinyl alcohols or acetates, styrene and siloxanes.

In a thirteenth aspect, the present invention consists in incorporation of fimbrolides either in surface coatings or polymers through the newly introduced functionality on the alkyl chain or the alkyl chain itself via direct polymerisation or copolymerisation with suitable monomers.

In an fourteenth aspect, the present invention consists in a fimbrolide derivative produced by the method according to the first, third, fifth, seventh, ninth, or eleventh aspects of the present invention.

In a fifteenth aspect, the present invention consists in the use of a fimbrolide derivative according to the present invention. The present inventors have found that many of the fimbrolide derivatives having the formula (II), (III), (IV), (V), (VI) and (VII) have antimicrobial and/or antifouling properties. Accordingly, the fimbrolide derivatives are suitable for use as antimicrobial and/or antifouling agents.

In a sixteenth aspect, the present invention provides methods of use of fimbrolides of formula II in medical, scientific and/or biological applications.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

MODES FOR CARRYING OUT THE INVENTION

Figure 1:
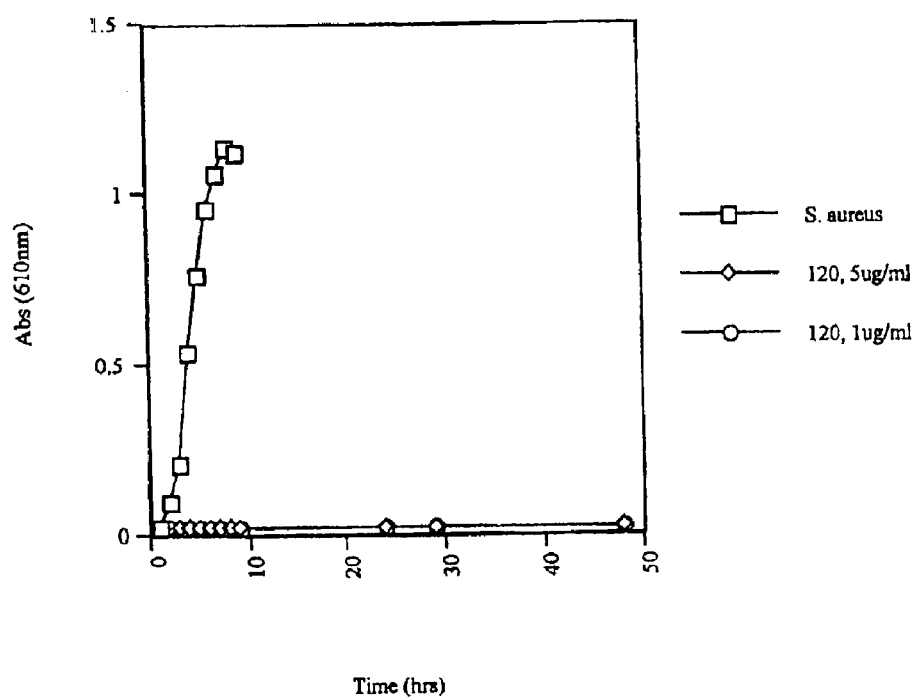
FIG. 1 is a graph showing growth of *Staphylococcus aureus* against compound 120.

The invention is further described in and illustrated by the following examples. The examples are not to be construed as limiting the invention in any way.

Experimental Details

General. Melting points are uncorrected. Microanalyses were performed by Dr H. P. Pham of The University of New South Wales Microanalytical Laboratory. $^1$H NMR spectra were obtained in $CDCl_3$ on a Bruker AC300F (300 MHz) or a Bruker DMX500 (500 MHz) spectrometer. $^{13}$C NMR were obtained in the same solvent on a Bruker AC300F (75.5 MHz) or a Bruker DMX500 (125.8 MHz) spectrometer. Chemical shifts were measured on the $\delta$ scale internally referenced to the solvent peaks: $CDCl_3$ ($\delta$ 7.26, $\delta$ 77.04). Ultraviolet spectra were measured on an Hitachi U-3200 spectrophotometer and refer to solutions in absolute MeOH. Infrared spectra were recorded on a Perkin-Elmer 298 or a Perkin-Elmer 580B spectrophotometer and refer to paraffin mulls. The electron impact mass spectra were recorded on an VG Quattro mass spectrometer at 70 eV ionisation voltage and 200° C. ion source temperature. FAB spectra were recorded on an AutoSpecQ mass spectrometer. Column chromatography was carried out using Merck silica gel 60H (Art. 7736), whilst preparative thin layer chromatography was performed on 2 mm plates using Merck silica gel 60GF$_{254}$ (Art. 7730).

General Method A:—for the synthesis of 4-oxo-2-alkenoic acids

Orthophosphoric acid (30 ml) was added to a mixture of glyoxylic acid (0.21 mol) and an alkanone (0.63 mol). The mixture was heated in an oil bath maintained at 80–85° C. for 4 h and then stirred at room temperature overnight. The mixture was extracted with dichloromethane/diethyl ether (1:1, 3×100 ml). The combined organic phase was washed with brine (3×75 ml), dried over sodium sulfate and evaporated to yield a dark brown oil. The crude product was chromatographed on a silica gel column using initially dichloromethane/light petroleum (1:1) to remove the unreacted alkanone followed by ethyl acetate/dichloromethane (1:1) to yield the 4-oxo-2-alkenoic acid as a pale yellow oil that solidified on keeping at room temperature.

The following compounds were prepared according to method A.

4-Oxo-2-pentenoic acid

Prepared from glyoxylic acid (40 g, 0.44 mol), acetone (60 g, 1.00 mol) and orthophosphoric acid (85%, 60 ml) Pale yellow prisms (10.5 g, 20%). m.p. 120–121° C. (lit m.p. 121–122° C.).

3-Methyl-4-oxo-2-pentenoic acid

Prepared from glyoxylic acid (16.1 g, 0.18 mol), 2-butanone (45.6 g, 0.63 mol) and orthophosphoric acid (30 ml). $^1$H n.m.r. $\delta$ ($CDCl_3$) 2.07, s, 3H, $CH_3$; 2.40, s, $CH_3$; 6.57, s, 1H, H2. $^{13}$C n.m.r. $\delta$ ($CDCl_3$): 13.2, $CH_3$; 26.2, $CH_3$; 125.2, C2; 152.6, C3; 171.2, C1; 199.8, C4.

3-Propyl-4-oxo-2-pentenoic acid

Prepared from glyoxylic acid (15.2 g, 0.17 mol), 2-hexanone (30 g, 0.3 mol) and orthophosphoric acid (30 ml). $^1$H n.m.r. $\delta$ ($CDCl_3$) 0.88, t J 7.2 Hz, 3H, $CH_3$; 1.44, m, 2H, $CH_2$; 2.41, s, 3H, $CH_3$; 2.78, t J 7.5 Hz, 2H, $CH_2$; 6.51, s, CH $^{13}$C n.m.r. $\delta$ ($CDCl_3$): 14.0, $CH_3$; 22.5, 26.5, $CH_2$; 28.6, $CH_3$; 124.5, C2; 157.3, C3; 170.4, COOH; 199.8 C2.

3-Butyl-4-oxo-2-pentenoic acid

Prepared from glyoxylic acid (15.2 g, 0.17 mol), 2-heptanone (34.2 g, 0.3 mol) and orthophosphoric acid (30 ml). $^1$H n.m.r. $\delta$ ($CDCl_3$) 0.91, t J 7.2 Hz, 3H, $CH_3$; 1.38, m, 4H, $CH_2$; 2.39, s, 3H, $CH_3$; 2.77, t J 7.2 Hz, 2H, $CH_2$; 6.49, s, CH.

3-Hexyl-4-oxo-2-pentenoic acid

Prepared from glyoxylic acid (5.35 g, 7.0 mmol), 2-nonanone (14.2 g, 1.0 mol) and orthophosphoric acid (20 ml). $v_{max}$ 2925, 2850, 1700, 1450, 1410, 1350, 1220, 1120, 870, 770, 720 cm$^{-1}$. $^1$H n.m.r. δ (CDCl$_3$) 0.87, t J 7.2 Hz, 3H, CH$_3$; 1.29, m, 8H, CH$_2$; 2.39, s, 3H, CH$_3$; 2.77, t J 6.8 Hz, 2H, CH$_2$; 6.50, s, CH.

3-Heptyl-4-oxo-2-pentenoic acid

Prepared from glyoxylic acid (5.10 g, 6.7 mmol), 2-decanone (15.0 g, 9.6 mmol) and orthophosphoric acid (20 ml). $v_{max}$ 2925, 2820, 1690, 1460, 1380, 1240, 1120, 880, 720 cm$^{-1}$. $^1$H n.m.r. δ (CDCl$_3$) 0.87, t J 7.2 Hz, 3H, CH$_3$; 1.29, m, 10H, CH$_2$; 2.39, s, 3H, CH$_3$; 2.77, t J 6.8 Hz, 2H, CH$_2$; 6.50, s, CH. $^{13}$C n.m.r. δ (CDCl$_3$): 13.9, CH$_3$; 22.5, 26.6, 26.9, 29.1, 29.6, 31.6 CH$_2$; 28.8, CH$_3$; 124.3, C2; 157.9, C3; 170.9, COOH; 199.9 C2.

3-Decyl-4-oxo-2-pentenoic acid

Prepared from glyoxylic acid (4.94 g, 6.5 mmol), 2-tridecanone (12.9 g, 6.5 mmol) and orthophosphoric acid (20 ml). $^1$H n.m.r. δ (CDCl$_3$) 0.87, t J 7.2 Hz, 3H, CH$_3$; 1.30, m, 16H, CH$_2$; 2.39, s, 3H, CH$_3$; 2.77, t J 7.0 Hz, 2H, CH$_2$; 6.50, s, CH.

3-Methyl-4-oxo-2-hexenoic acid

Prepared from glyoxylic acid (16.1 g, 0.18 mol), 3-pentanone (45.6 g, 0.63 mol) and orthophosphoric acid (30 ml). $^1$H n.m.r. δ (CDCl$_3$) 1.23, t J 7.2 Hz, 3H, CH$_3$; 2.56, s, 3H, CH$_3$; 2.76, q J 7.2 Hz, CH$_2$; 6.55, s, CH.

2-Methyl-4-oxo-2-pentenoic acid and 3,5-dimethyl-5-hydroxy-2-(5H)furanone

Orthophosphoric acid (30 ml) was added dropwise to a mixture of pyruvic acid (12.7 g, 0.14 mol) and dry A.R. grade acetone (25 g, 0.54 mol). The mixture was heated under reflux in an oil bath maintained at 80–85° C. for 5 h and then stirred at room temperature for 72 h. The mixture was extracted with dichloromethane/diethyl ether (1:1, 3×100 ml). The combined organic phase was washed with brine (3×75 ml), dried over sodium sulfate and evaporated to yield a dark brown oil (12.7 g). The crude product was chromatographed on a silica gel column using initially dichloromethane as the eluent to yield 3,5-dimethyl-5-hydroxy-2-(5H)-furanone (3.2 g, 25%) ($^1$H n.m.r. δ (CDCl$_3$) 1.67, s, 3H, CH$_3$; 1.91, d J 1.5 Hz, CH$_3$; 3.41, bs, 1H, OH; 6.85, q J 1.5 Hz, H4. $^{13}$C n.m.r. δ (CDCl$_3$): 10.2, CH$_3$; 24.5, CH$_3$; 104.6, C5; 131.3, C3; 148.0, C4; 172.3, C2.) followed by ethyl acetate/dichloromethane (1:1) to yield the 2-methyl-4-oxo-2-pentenoic acid (2.6 g, 20%) as a pale yellow oil which solidified on keeping at room temperature.

4-Oxo-3-phenyl-2-pentenoic acid and 5-hydroxy-5-methyl-4-phenyl-2-(5H)-furanone

Orthophosphoric acid (30 ml) was added dropwise to a mixture of glyoxylic acid (15.2 g, 0.20 mol) and benyl methyl ketone (40.2 g, 0.30 mol). The mixture was heated in an oil bath maintained at 80–85° C. for 4 h and then stirred at room temperature for 24 h. The mixture was poured onto brine (100 ml) and extracted with dichloromethane/diethyl ether (1:1, 2×150 ml). The combined organic phase was washed with brine (3×75 ml), dried over sodium sulfate and evaporated to yield a brown viscous oil (30 g). Light petroleum (100 ml, 60–80° C.) was added to the viscous oil and the mixture cooled in an ice bath for 2 h The resulting solid was collected, washed with saturated sodium bicarbonate solution (75 ml), water and recrystallised form dichloromethane/light petroleum to yield 5-hydroxy-5-methyl-4-phenyl-2-(5H)-furanone (8.9 g, 21%) as a colourless needles. $^1$H n.m.r. δ (CDCl$_3$) 1.81, s, 3H, CH$_3$; 6.25, s, H3; 7.47, m, 3H, ArH; 7.80, m, 2H, ArH. $^{13}$C n.m.r. δ (CDCl$_3$): 25.1, CH$_3$; 107.3, C5; 114.3, C4; 128.2, 128.9, 129.0, 131.3, ArH; 166.1, C3; 171.0, C2. The bicarbonate extract was acidified with hydrochloric acid (6N) and extracted with dichloromethane (3×75 ml). The combined extract was washed with brine, dried over anhydrous sodium sulfate and evaporated to yield 2-methyl-4-oxo-2-pentenoic acid (8.7 g, 23%) as a pale yellow oil that solidified on keeping at room temperature. $^1$H n.m.r. δ (CDCl$_3$) 2.27, s, CH$_3$; 6.70, s, 1H, H4, 7.18, m, 2H, ArH; 7.47, m, 3H, ArH. $^{13}$C n.m.r. δ (CDCl$_3$): 28.0, CH$_3$; 125.2, C2; 128.9, 129.0, 129.4, 131.3, ArH; 152.5, C3; 169.7, C1; 199.3, C4.

General Methods for the Synthesis of Halogenated 4-Oxoalkanoic Acids

Examples of the prepararation of 2,3-dibromo-4-oxoalkanoic acids, and 3,5-dibromo- and 3,5,5-tribromolevulinic acids are provided below.

General Method B:—for the synthesis of 2,3-dibromo-4-oxoalkanoic acids

A solution of bromine (0.045 mol) in dry dichloromethane (8 ml) was added slowly to an ice-cooled solution of 4-oxo-2-alkenoic acid (0.03 mol) in dry dichloromethane (30 ml). The mixture was stirred in an ice-bath for 0.5 h and then at room temperature for 0.5 h. The resulting solution was washed with aqueous sodium metabisulfite (0.5 M, 30 ml) and brine (30 ml). The solution was dried over sodium sulfate and evaporated to dryness to yield the crude 2,3-dibromo-4-oxoalkanoic acid as a pale brown oil (60–65%).

The crude product was used for the lactonisation step without further purification.

2,3-Dibromo-4-oxopentanoic acid

4-Oxo-2-pentenoic acid afforded a pale yellow oil (0.93 g, 39%) as a mixture of diastereoisomers. $^1$H n.m.r. δ (CDCl$_3$) 2.42, s, 3H, CH$_3$; 2.44, s, 3H, CH$_3$; 4.65–4.74, m, H2 and H3; 6.32, broad s, COOH. $^{13}$C n.m.r. δ(CDCl$_3$): 27.2, 27.5, CH$_3$; 40.0, 45.1, C2; 46.6, 52.0, C3; 171.2, 172.3, C1; 196.9, 200.3, C4.

2,3-Dibromo-3-methyl-4-oxopentanoic acid

3-Methyl-4-oxo-2-pentenoic acid (5 g, 39 mmol) and bromine (7.5 g, 46.9 mmol) in dichloromethane (100 ml) gave a mixture of diastereoisomers as a pale yellow oil (8.2 g, 75%). $^1$H n.m.r. δ (CDCl$_3$): 2.18, bs, 3H, CH$_3$; 2.20, bs, 3H, CH$_3$; 5.01, s, 1H, H2; 5.08, s, 1H, H2; 6.00, bs, COOH. $^{13}$C n.m.r. δ (CDCl$_3$): 22.5, 24.0, 24.2, 25.1, CH$_3$; 52.3, 53.4, C2; 61.8, 65.3, C3; 171.8, 172.8, C1; 198.9, 201.4, C4.

2,3-Dibromo-3-butyl-4-oxopentanoic acid

3-Butyl-4-oxo-2-pentenoic acid (2.00 g, 13.0 mmol) and bromine (3.2 g, 20 mmol) in dichloromethane (35 ml) gave a mixture of diastereoisomers as a colourless oil (3.7 g, 92%). $^1$H n.m.r. δ (CDCl$_3$) 0.93, m, 3H, CH$_3$; 0.95, m, 3H, CH$_3$; 1.42, broad m, CH$_2$; 1.87, broad m, CH$_2$; 2.18, bs, 3H, CH$_3$; 2.54, broad m, CH$_2$; 4.87, bs, 1H, H2; 5.00, s, 1H, H2; 7.4, bs, COOH.

2,3-Dibromo-3-hexyl-4-oxopentanoic acid

3-Hexyl-4-oxo-2-pentenoic acid (2.12 g, 13.4 mmol) and bromine (2.4 g, 15 mmol) in dichloromethane (35 ml) gave a mixture of diastereoisomers as a colourless oil (3.4 g, 87%). $^1$H n.m.r. δ (CDCl$_3$) 0.88, t, J 7.1 Hz, 3H, CH$_3$; 0.90, t, J 7.1 Hz, 3H, CH$_3$; 1.33, broad m, CH$_2$; 1.50–1.67, broad m, CH$_2$; 2.00–2.30, m, CH$_2$; 2.54, s, CH$_3$; 2.57, s, CH$_3$; 4.83, s, 1H, H2; 5.00, s, 1H, H2.

2,3-Dibromo-3-heptyl-4-oxopentanoic acid

3-Heptyl-4-oxo-2-pentenoic acid (1.1 g, 5.0 mmol) and bromine (1.2 g, 7.0 mmol) in dichloromethane (35 ml) gave a mixture of diastereoisomers as a colourless oil (1.6 g, 80%). $^1$H n.m.r. δ (CDCl$_3$) 0.88, broad t, 3H, CH$_3$; 1.28, broad m, CH$_2$; 1.50–1.67, broad m, CH$_2$; 2.00–2.30, m, CH$_2$; 2.54, s, CH$_3$; 2.57, s, CH$_3$; 4.87, s, 1H, H2; 4.99, s, 1H, H2.

2,3-Dibromo-3-methyl-4-oxohexanoic acid

3-Methyl-4-oxo-2-hexenoic acid (1.01 g, 7.1 mmol) and bromine (1.7 g, 10.7 mmol) in dichloromethane (35 ml) gave a mixture of diastereoisomers as a pale yellow oil (1.7 g, 75%). $^1$H n.m.r. δ (CDCl$_3$) 1.16, t J 7.1 Hz, H6, 1.18, t J 7.1 Hz, H6, 2.17, q J 7.1 Hz, H5; 2.18, q J 7.1 Hz, H5; 2.19, bs, 3H, CH$_3$; 2.20, bs, 3H, CH$_3$; 5.03, s, 1H, H2; 5.14,s, 1H, H2.

2,3,5-Tribromo-4-oxopentanoic acid

A solution of bromine (10 g, 0.06 mol) in dry dichloromethane (8 ml) was added slowly to an ice-cooled solution of 4-oxo-2-pentenoic acid (3.6 g, 0.03 mol) in dry dichloromethane (30 ml). The mixture was stirred at room temperature for 0.5 h and then at reflux for 1 h. After cooling to room temperature, the resulting solution was washed with aqueous sodium metabisulfite (0.5 M, 30 ml) and brine (30 ml). The solution was dried over sodium sulfate and evaporated to dryness to yield the crude 2,3,5-tribromo-4-oxopentanoic acid a pale brown oil (7.2 g, 65%). $^1$H n.m.r. δ (CDCl$_3$) 4.06, d, J 12.4 Hz, H$_a$5; 4.27, d, J 12.4 Hz, H$_b$5; 4.67, d, J 11.3 Hz, H2; 5.20, d, J 11.3 Hz, H3.

Synthesis of 3,5-dibromo-4-oxopentanoic acid

A solution of bromine (70 g, 0.44 mol) in dry dichloromethane (80 ml) was added slowly to a solution of 4-oxopentanoic acid (23.2 g, 0.2 mol) in dry dichloromethane (700 ml) containing hydrobromic acid (33% in acetic acid, 12 drops). The mixture was warmed at 50° C. for 0.5 h, and then at reflux for 1 h. It was cooled to room temperature and the resulting solution was washed successively with water (100 ml), aqueous sodium metabisulfite (0.5 M, 100 ml) and brine (100 ml). The organic phase was dried over sodium sulfate, and evaporated to dryness to yield the crude 3,5-dibromo-4-oxopentanoic acid as a white solid. The crude product was recrystallised from chloroform to yield the acid as colourless needles (44 g, 76%) m.p. 112–113° C. (lit. m.p. 113° C.).

Synthesis of 3,5,5-tribromo-4-oxopentanoic acid

A solution of bromine (43 g, 0.27 mol) in dry dichloromethane (80 ml) was added slowly to a solution of 4-oxopentanoic acid (10 g, 0.90 mol) in dry dichloromethane (70 ml) containing hydrobromic acid (33% in acetic acid, 12 drops). The mixture was warmed at 50° C. for 0.5 h, and then at reflux for 1 h. It was cooled to room temperature and the resulting solution was washed successively with water (100 ml), aqueous sodium metabisulfite (0.5 M, 100 ml) and brine (100 ml). The solution was dried over sodium sulfate and evaporated to dryness to yield the crude 3,5,5-tribromo-4-oxopentanoic acid as a yellow oil. $^1$H n.m.r. δ (CDCl$_3$) 3.13, dd, J 6.8 Hz 17.7 Hz, H$_a$2; 3.41, dd, J 6.8 Hz 17.7 Hz, H$_b$2; 5.18, dd, J 6.8, 6.8 Hz, H3; 6.47, s, H5.

The corresponding alkyl substituted di- and tri-brominated 4-oxopentanoic acids were similarly prepared.

General Methods for the Synthesis of Halogenated 2-Tetrahydrofuranones

Examples of the preparation of 3,4-dibromo-4-alkyl-5-(methylene)-, 4-bromo-5-(bromomethylene)-, 3-alkyl-4-bromo-5-(dibromomethylene)-, and 3-alkyl-3,4-dibromo-5-(alkylidene)-2(5H)-tetrahydrofuranone are provided below.

General Method C:—for the synthesis of 3,4-dibromo-4-alkyl-5-(methylene)-, 2-tetrahydrofuranones 3,4-Dibromo-4-alkyl-5-(methylene)-2-tetrahydrofuranone Phosphorus pentoxide (11.4 g) was added with stirring to a solution of 2,3-dibromo-3-alkyl-4-oxopentanoic acid (4.6 g, 16.0 mmol) in dry dichloromethane (25 ml). The mixture was heated at reflux with stirring for 2 h, and cooled to room temperature. The resulting mixture was filtered through a pad of celite, washed with brine, dried over sodium sulfate and evaporated to yield the tetrahydrofuranone as a pale yellow oil (60–80%).

This product was used in the next step without further purification.

Method C was used to prepare the following compounds.

3,4-Dibromo-4-methyl-5(methylene)-2-tetrahydrofuranone

Colourless oil (85%) as a mixture of diastereoisomers. $^1$H n.m.r. δ (CDCl$_3$) 2.10, s, 3H, CH$_3$; 2.17, s, 3H, CH$_3$; 4.48, s, H3; 4.77, s, H3; 4.89, d, J 3.8 Hz, CH$_a$; 4.92, d, J 3.8 Hz, CH$_b$; 5.02, d, J 3.8 Hz, CH$_a$; 5.08, d, J 3.8 Hz, CH$_b$.

3,4-Dibromo-4-propyl-5-(methylene)-2-tetrahydrofuranone

Pale yellow oil (62%) as a mixture of diastereoisomers. $^1$H n.m.r. δ (CDCl$_3$) 1.01, t, 3H, CH$_3$; 1.05, m, 3H, CH$_3$; 1.62, m, 2H, CH$_2$; 1.65, m, 2H, CH$_2$; 2.45, m, 2H, CH$_2$; 2.47, m, 2H, CH$_2$; 4.66, s, H3; 4.71, s, H3; 4.90, d, J 3.3 Hz, CH$_a$; 4.91, d, J 3.7 Hz, CH$_b$; 4.91, d, J 3.3 Hz, CH$_a$; 5.04, d, J 3.7 Hz, CH$_b$.

3,4-Dibromo-4-butyl-5-(methylene)-2-tetrahydrofuranone

Pale yellow oil (58%) as mixture of diastereoisomers. $^1$H n.m.r. δ (CDCl$_3$) 0.98, t, 3H, CH$_3$; 1.00, t, 3H, CH$_3$; 142, m, 2H, CH$_2$; 1.69, m, 2H, CH$_2$; 2.28, m, 2H, CH$_2$; 4.66, s, H3; 4.71, s, H3; 4.86, d, J 3.8 Hz, CH$_a$; 4.88, d, J 3.7 Hz, CH$_b$; 5.03, d, J 3.7 Hz, CH$_a$; 5.05, d, J 3.7 Hz, CH$_b$.

3,4-Dibromo-4-hexyl-5-(methylene)-2-tetrahydrofuranone

Pale yellow oil (89%) as a mixture of diastereoisomers. $^1$H n.m.r. δ (CDCl$_3$) 0.92, t, 3H, CH$_3$; 1.35, m, 6CH$_2$; 1.76, m, 2H, CH$_2$; 2.23, m, 2H, CH$_2$; 4.62, s, H3; 4.66, s, H3; 4.87, d, J 3.2 Hz, CH$_a$; 4.88, d, J 3.2 Hz, CH$_b$; 5.03, d, J 3.2 Hz, CH$_a$; 5.05, d, J 3.2 Hz, CH$_b$.

3,4-Dibromo-4-heptyl-5-(methylene)-2-tetrahydrofuranone

Pale yellow oil (59%) as mixture of diastereoisomers. $^1$H n.m.r. δ (CDCl$_3$) 0.90, t, 3H, CH$_3$; 1.32, m, 8H, CH$_2$; 1.76, m, 2H, CH$_2$; 2.30, m, 2H, CH$_2$; 4.63, s, H3; 4.66, s, H3; 4.86, d, J 3.8 Hz, CH$_a$; 4.87, d, J 3.8 Hz, CH$_b$; 5.02, d, J 3.8 Hz, CH$_a$; 5.04, d, J 3.8 Hz, CH$_b$.

Synthesis of 3,4-dibromo-3-ethyl-5-(ethylidene)-2-tetrahydrofuranone

Pale yellow oil (3.68 g, 84%) as a mixture of diastereoisomers. $^1$H n.m.r. δ (CDCl$_3$) 1.91, d, J 7.1 Hz, 5-(CHMe); 1.92, d, J 7.1 Hz, 5-(CHMe); 2.03, s, 3H, CH$_3$; 2.12, s, 3H, CH$_3$; 4.48, s, H4; 4.76, s H4; 5.34, q, 1H, 5-(CHMe); 5.36, q, 1H, 5-(CHMe).

Synthesis of 4-bromo-5-(bromomethylene)-2-tetrahydrofuranone

Phosphorus pentoxide (22.5 g) was added with stirring to a solution of 3,5-dibromo-4-oxopentanoic acid (30.4 g, 0.11 mol) in dry dichloromethane (500 ml). The mixture was heated at reflux with stirring for 2 h, and cooled to room temperature. The resulting mixture was filtered through a pad of filter aid, washed with brine, dried over sodium sulfate and evaporated to yield the tetrahydrofuranone (mixture of Z- and E-isomers in 4:1 ratio) as a pale yellow oil (23.4 g, 82%). The oil solidified on standing at room temperature overnight. Crystallisation from dichloromethane/light petroleum (60–80° C.) gave an analytically pure sample of the Z-isomer. m. p. 79° C. ν$_{max}$ 3094, 3027, 2947, 1799, 1634, 1393, 1289, 1114, 949, 838, 747, 718, 660 cm$^{-1}$. λ$_{max}$ 279 nm (ε 4938). $^1$H n.m.r. δ (CDCl$_3$) 3.10, dd, J 2.3 Hz, 18.8 Hz, H$_a$3; 3.45, dd, J 7.9 Hz, 18.8 Hz, H$_b$3; 5.07, m, H4; 5.90, s, 5-CHBr. $^{13}$C n.m.r. δ (CDCl$_3$): 37.2, C3; 40.5, C4; 86.9, 5-CHBr, 152.3, C5; 169.5, C2.

E-isomer: $^1$H n.m.r. δ (CDCl$_3$) 3.09, dd, J 2.3 Hz, 18.8 Hz, H$_a$3; 3.38, dd, J 7.9 Hz, 18.8 Hz, H$_b$3; 5.15, m, H4; 6.19, s, 5-CHBr. $^{13}$C n.m.r. δ (CDCl$_3$): 37.0, C3; 39.8, C4; 90.1, 5-CHBr; 151.9, C5; 170.4, C2.

Synthesis of 4-bromo-3-butyl-5-(dibromomethylene)-2-tetrahydrofuranone

Phosphorus pentoxide (10.0 g) was added with stirring to a solution of 2-(1,3,3-tribromo-2-oxopropyl)hexanoic acid (7.7 g, 0.11 mol) in dry dichloromethane (150 ml). The mixture was heated at reflux with stirring for 2 h, and cooled to room temperature. The resulting mixture was filtered through a pad of filter aid, washed with brine, dried over sodium sulfate and evaporated to yield the tetrahydrofuranone as a pale brown oil (7.0 g, 82%) that solidified on standing at 4° C. overnight. $v_{max}$ 2958, 2930, 2871, 1820, 1782, 1638, 1455, 1127, 1086, 965, 849, 757, 718 cm$^{-1}$. $^1$H n.m.r. δ (CDCl$_3$) 0.93, t, J 6.7 Hz, (H4')$_3$; 1.37–1.81, m, (H3')$_2$-(H1')$_2$; 3.22, t, J 7.5 Hz, H3; 4.79, s, H4. $^{13}$C n.m.r. δ (CDCl$_3$): 14.1, C4'; 22.5, C3'; 28.9, C1'; 31.6, C2'; 43.6, C4; 53.7, C3; 76.5, 5-CBr$_2$; 149.8, C5; 172.5, C2.

General Methods for the Synthesis of Halogenated 2(5H)-Furanones

Examples of the preparation of 3-bromo-4-alkyl-5-methylene)-2(5H)-furanone, 5-(bromomethylene)-2(5H)-, 5-(dibromomethylene)-2(5H)- and 3-alkyl-5-(bromomethylene)-2(5H)-tetrahydrofuranone are provided below.

General Method Part D:—for the synthesis of 3-bromo-4-alkyl-5-(methylene)-2(5H)-furanones 1,8-Diazabicyclo[5.4.0]undec-7-ene (DBU/DABCO or DMAP) (14.8 mmol) was added dropwise to a cooled stirred solution of 3,4-dibromo-4-alkyl-5-(methylene)-2-tetrahydrofuranone (0.016 mol) in dichloromethane (30 ml). The mixture was stirred at room temperature for 0.5 h, washed with dilute hydrochloric acid (2N, 20 ml), brine (20 ml), dried over sodium sulfate, and evaporated to dryness. The crude product was passed through a short plug of silica gel to yield the 3-bromo-4-methyl-5-(methylene)-2(5H)-furanone (50–83%) as a colourless oil.

3-Bromo-4-methyl-5(methylene)-2(5H)-furanone

Pale brown oil (65%). $^1$H n.m.r. δ (CDCl$_3$) 2.17, s, 3H, CH$_3$; 5.01, d, J 3.0 Hz, CH$_a$; 5.22, d, J 3.0 Hz, CH$_b$.

3-Bromo-4-propyl-5-(methylene)-2(5H)-furanone

Pale brown oil (69%). $^1$H n.m.r. δ (CDCl$_3$) 1.02, t, J 7.1 Hz 3H, CH$_3$; 1.68, m, 2H, CH$_2$; 2.52, t, J 7.1 Hz, 2H, CH$_2$; 5.01, d, J 3.1 Hz, CH$_a$; 5.24, d, J 3.1 Hz, CH$_b$.

3-Bromo-4-butyl-5-(methylene)-2(5H)-furanone

Pale brown oil (58%). $^1$H n.m.r. δ (CDCl$_3$) 0.96, t, J 7.2 Hz, 3H, CH$_3$; 1.37, m, 2H, CH$_2$; 1.64, m, 2H, CH$_2$; 2.52, t, J 7.3 Hz, 2H, CH$_2$; 5.02, d, J 3.1 Hz, CH$_a$; 5.24, d, J 3.1 Hz, CH$_b$.

3-Bromo-4-hexyl-5-(methylene)-2(5H)-furanone

Pale brown oil (73%). $^1$H n.m.r. δ (CDCl$_3$) 0.93, t, J 7.1 Hz, 3H, CH$_3$; 1.35, m, 6H, CH$_2$; 1.62, m, 2H, CH$_2$; 2.53, m, 2H, CH$_2$; 5.01, d, J 3.0 Hz, CH$_a$; 5.24, d, J 3.0 Hz, CH$_b$.

3-Bromo-4-heptyl-5-(methylene)-2(5H)-furanone

Pale brown oil (82%). $^1$H n.m.r. δ (CDCl$_3$) 0.89, t, J 7.3 Hz, 3H, CH$_3$; 1.29, m, 8H, CH$_2$; 1.61, m, 2H, CH$_2$; 2.53, t, J 7.5 Hz, 2H, CH$_2$; 5.02, d, J 3.2 Hz, CH$_a$; 5.24, d, J 3.2 Hz, CH$_b$. $^{13}$C n.m.r. δ (CDCl$_3$): 13.9, CH$_3$; 22.5, 26.2, 28.1, 28.8, 29.1, 31.5, CH$_2$; 95.3, 5-(CH$_2$); 112.2, C3; 154.3, C5; 154.6, C4; 164.6, C2.

Synthesis of 5-(bromomethylene)-2(5H)-furanone 1,4-Diazabicyclo[2.2.2]octane (DABCO) (2.8 g, 0.025 mol) was added to a stirred solution of a mixture of (E) and (Z)-isomers of 4-bromo-5-(bromomethylene)-tetrahydro-2-furanone (4.2 g, 0.016 mol) in dichloromethane (20 ml). The mixture was stirred at room temperature for 2 h and filtered. The filtrate was washed with dilute hydrochloric acid (2N, 10 ml), brine (20 ml), dried over sodium sulfate, and evaporated to dryness. The crude product was recrystallised from light petroleum (60–80° C.) to yield 5-(bromomethylene)-2(5H)-furanone as colourless needles (2.2 g, 76%) m.p. 80–82° C. $v_{max}$ 2905, 2840, 1770, 1740, 1630, 1540, 1450, 1370, 1290, 1160, 1100, 1070, 915, 880, 815, 770, 720 cm$^{-1}$. $\lambda_{max}$ 284 nm (ε 13535). $^1$H n.m.r. δ (CDCl$_3$) 6.12, s, 5-CHBr; 6.32, d, J 5.1 Hz, H3; 7.40, d, J 5.1 Hz, H4. $^{13}$C n.m.r. δ (CDCl$_3$): 92.5, 5-CHBr; 120.7, C3; 141.8, C4; 152.4, C5; 168.3, C2. Mass spectrum: m/z 176 (M ($^{81}$Br), 100%); 174 (M ($^{79}$Br), 100); 148 (44); 142 (40); 122 (26); 120 (24); 95 (30).

Synthesis of 3-butyl-5-(dibromomethylene)-2(5H)-furanone 1,4-Diazabicyclo[2.2.2]octane (DABCO) (1.2 g, 10.4 mmol) was added to a stirred solution of 4-bromo-3-butyl-5-(dibromomethylene)-tetrahydro-2(5H)-furanone (2.0 g, 6.9 mmol) in dichloromethane (20 ml). The mixture was stirred at room temperature for 2 h and filtered. The filtrate was washed successively with dilute hydrochloric acid (2N, 10 ml), brine (20 ml). It was dried over sodium sulfate and evaporated to dryness to yield the furanone as pale brown solid. The crude product was recrystallised from light petroleum (60–80° C.) containing a small amount of dichloromethane to yield 3-butyl-5-(dibromomethylene)-2(5H)-furanone as a white solid (1.0 g, 63%). m.p. 48–49° C. $v_{max}$ 3080, 2900, 2840, 1740, 1590, 1445, 1330, 1255, 1040, 960, 890, 840, 820, 705 cm$^{-1}$. $\lambda_{max}$ 303 nm (ε 13682). $^1$H n.m.r. δ (CDCl$_3$) 0.92, t, J 7.2 Hz, (H4')$_3$; 1.32, m, (H3')$_2$; 1.56, m, (H2')$_2$; 2.32, t, J 7.3 Hz, (H1')$_2$; 7.27, br s, H4. $^{13}$C n.m.r. δ (CDCl$_3$): 13.7, C4'; 22.3, C3'; 25.4, C1'; 29.3, C2'; 78.8, 5-CBr$_2$; 134.0, C4; 138.0, C3, 149.7, C5; 166.7, C2. Mass spectrum: m/z 312 (M ($^{81}$Br$_2$), 7%); 310 (M ($^{81}$Br, $^{79}$Br), 14); 308 (M, 7); 283 (6); 281 (12); 279 (7); 270 (19); 268 (35), 266 (20); 231 (72); 229 (72); 202 (16); 200 (32); 198 (16); 189 (30); 187 (30); 172 (16); 161 (14); 159 (14); 149 (28).

One pot syntheses of 3-bromo-4-alkyl-5-(methylene)-2(5H)-furanone, 5-(bromomethylene)-2(5H)-, 5-(dibromomethylene)-2(5H)- and 3-alkyl-5-(bromomethylene)-2(5H)-furanones The general methods C and D were carried out in one sequence without the isolation and purification of intermediates.

Synthesis of 3-Bromo-4-methyl-5-(methylene)-2(5H) furanone

Phosphorus pentoxide (11.5 g) was added with stirring to a solution of 2,3-dibromo-3-methyl-4-oxopentanoic acid (4.6 g, 16.0 mmol) in dry dichloromethane (30 ml). The mixture was heated at reflux with stirring for 2 h. It was cooled to room temperature and the resulting mixture was filtered through a pad of filter aid and treated with 1,4-diazabicyclo[2.2.2]octane (DABCO) (2.24 g, 14.8 mmol). The mixture was stirred at room temperature for 1 h, washed with dilute hydrochloric acid (2N, 10 ml), brine (20 ml), dried over sodium sulfate, and chromatographed on a short plug of silica gel to yield the 3-bromo-4-methyl-5-(methylene)-2(5H)furanone as a colourless oil (2.14 g, 83%).

Synthesis of 5-(bromomethylene)-2(5H)-furanone

Phosphorus pentoxide (22.5 g) was added with stirring to a solution of 3,5-dibromo-4-oxopentanoic acid (30.4 g, 0.11 mol) in dry dichloromethane (500 ml). The mixture was heated at reflux with stirring for 2 h. It was cooled to room temperature and the resulting mixture was filtered through a pad of filter aid and treated with 1,4-diazabicyclo[2.2.2] octane (DABCO) (2.8 g, 0.025 mol). The mixture was stirred at room temperature for 2 h and filtered. The filtrate was washed with dilute hydrochloric acid (2N, 10 ml), brine (20 ml), dried over sodium sulfate, and evaporated to dryness. The crude product was recrystallised from light petroleum (60–80° C.) to yield the 5-(bromomethylene)-2(5H)-furanone as colourless needles (2.1 g, 73%) m.p. 82–83° C.

Synthesis of 5-(dibromomethylene)-2(5H-furanone

Phosphorus pentoxide (20 g) was added with stirring to a solution of 3,5,5-tribromo-4-oxopentanoic acid (14.5 g, 4.1 mmol) in dry dichloromethane (200 ml). The mixture was heated at reflux with stirring for 2 h, and cooled to room temperature. The resulting mixture was filtered through a pad of filter aid and the filtrate treated with a solution of 4-(dimethylamino)pyridine (DMAP) (5.8 g, 4.7 mmol) in dichloromethane (30 ml). The mixture was stirred at room temperature for 2 h and filtered. The filtrate was washed with dilute hydrochloric acid (2N, 10 ml), brine (20 ml), dried over sodium sulfate, and evaporated to dryness. The crude product was chromatographed on silica using light petroleum (60–80° C.) as the eluent to yield the 5-dibromomethylene)-2(5H)-furanone as pale yellow prisms. (4.2 g, 40%) m.p. 135° C. $v_{max}$ 2905, 2840, 1805, 1783, 1558, 1257, 1102, 1067, 960, 887, 826 cm$^{-1}$. $\lambda_{max}$ 306 nm ($\epsilon$ 4300). $^1$H n.m.r. $\delta$ (CDCl$_3$) 6.40, d, J 5.3 Hz, H3; 7.66, d, J 5.3 Hz, H4. $^{13}$C n.m.r. $\delta$ (CDCl$_3$): 81.7, 5-CBr$_2$; 122.3, C3; 140.6, C4; 150.7, C5; 167.6, C2. Mass spectrum: m/z 176 (M ($^{81}$Br), 100%); 174 (M ($^{79}$Br), 100).

General Methods for the Syntheses of Halogenated Haloalkyl-2(5H)-Furanones

Examples of the preparation of 5-bromomethyl)-3,5-dibromo- and 5-(dibromomethyl)-5-bromo-2(5H)-furanones are provided below.

General method E:—for the synthesis of 4-alkyl-5-(bromomethyl)-3,5-dibromo-, 4-alkyl-3,5-dibromo-5-(dibromomethyl)-, 4-alkyl-5-bromo-(bromomethyl)-5- and 4-alkyl-5-bromo-5-(dibromomethyl)-2(5H)-furanones A solution of bromine (17 mmol) in dichloromethane (10 ml) was added dropwise to an ice-cooled solution of 3-bromo-4-alkyl-5-methylene)-2(5H)-furanone (18.7 mmol) in dichloromethane (20 ml). The mixture was stirred in ice for 0.5 h and then at room temperature for further 1 h. It was washed with saturated sodium metabisulfite solution (30 ml) followed by brine (40 ml). The resulting solution was dried over anhydrous sodium sulfate and evaporated to yield the 3,5-dibromo-5-bromomethyl-4-alkyl-2(5H)-furanone (65–85%) as a colourless oil.

5-(Bromomethyl)-3,5-dibromo-4-methyl-2(5H)-furanone

Pale yellow solid (79%). $v_{max}$ 2925, 2850, 1780, 1650, 1430, 1380, 1295, 1260, 1160, 1130, 970, 850, 740 cm$^{-1}$. $^1$H n.m.r. $\delta$ (CDCl$_3$) 2.19, s, 3H, CH$_3$; 3.97, d, J 11.7 Hz, CH$_a$Br; 4.26, d, J 11.7 Hz, CH$_b$Br. $^{13}$C n.m.r. $\delta$ (CDCl$_3$): 12.9, CH$_3$; 33.8, CH$_2$Br; 90.9, C5; 112.3, C3; 161.5, C4; 163.6, C2. Mass spectrum: m/z 352 (M ($^{81}$Br$_3$), 4%); 350 (M ($^{81}$Br$_2$), ($^{79}$Br), 8%); 348 (M ($^{81}$Br), ($^{79}$Br$_2$), 8%); 346 (M ($^{79}$Br$_3$), 4%); 271 (40); 269 (80); 265 (40); 213 (10); 190 (70); 188 (70); 162 (20); 158 (20; 122 (40); 120 (40).

3,5-Dibromo-5-(dibromomethyl)-4-methyl-2(5H)-furanone

Colourless prisms (34%). $^1$H n.m.r. $\delta$ (CDCl$_3$) 2.26, s, 3H, CH$_3$; 5.91, s, 5-(CHBr$_2$). $^{13}$C n.m.r. $\delta$ (CDCl$_3$): 13.7, CH$_3$; 43.1, 5-(CHBr$_2$); 93.8, C5; 112.9, C3; 143.3, C4; 161.4, C2.

5-(Bromomethyl)-3,5-dibromo-4-butyl-2(5H)-furanone

Pale yellow oil (84%). $^1$H n.m.r. $\delta$ (CDCl$_3$) 1.00, t, J 7.3 Hz, 3H, CH$_3$; 1.45, m, 2H, CH$_2$; 1.80, m, 2H, CH$_2$; 2.45, t, J 7.1 Hz, 2H, CH$_2$; 4.00, d, J 10.7 Hz, CH$_a$Br; 4.28, d, J 11.7 Hz, CH$_b$Br. $^{13}$C n.m.r. $\delta$ (CDCl$_3$): 13.5, CH$_3$; 23.0, 27.5, 28.3, CH$_2$; 34.2, CH$_2$Br; 91.3, C5; 112.4, C3; 163.8, C4; 164.2, C2.

5-(Bromomethyl)-3,5-dibromo-4-hexyl-2(5H)-furanone

Pale yellow oil (85%). $^1$H n.m.r. $\delta$ (CDCl$_3$) 0.92, t J 7.1 Hz, 3H, CH$_3$; 1.35, m, 4H, CH$_2$; 1.46, m, 2H, CH$_2$; 1.82, m, 2H, CH$_2$; 2.47, t, J 8.1 Hz, 2H, CH$_2$; 4.00, d, J 11.7 Hz, CH$_a$Br, 4.27, d, J 11.7 Hz, CH$_b$Br.

5-(Bromomethyl)-3,5-dibromo-4-heptyl-2(5H)-furanone

Pale yellow oil (72%). $v_{max}$ 3038, 2953, 2927, 2855, 1793, 1635, 1463, 1415, 1377, 1265, 1227, 1165, 1129, 973, 881, 743 cm$^{-1}$. $\lambda_{max}$ 244 nm ($\epsilon$ 4330). $^1$H n.m.r. $\delta$ (CDCl$_3$) 0.90, t, J 7.1 Hz, 3H, CH$_3$; 1.32, m, 8H, CH$_2$; 1.82, m, 2H, CH$_2$; 2.47, t, J 8.1 Hz, 2H, CH$_2$; 4.00, d, J 11.7 Hz, CH$_a$Br; 4.27, d, J 11.7 Hz, CH$_b$Br. $^{13}$C n.m.r. $\delta$ (CDCl$_3$): 13.9, CH$_3$; 22.5, 26.3, 27.8, 28.6, 29.8, 31.5, CH$_2$; 34.2, CH$_2$Br; 91.3, C5; 112.4, C3; 163.8, C4; 164.3, C2.

5-(Dibromomethyl)-3,5-dibromo-4-heptyl-2(5H)-furanone

Pale yellow oil (52%). $v_{max}$ 3005, 2953, 2926, 2855, 1796, 1630, 1464, 1377, 1260, 1165, 1143, 968, 885, 799, 746, 720 cm$^{-1}$. $\lambda_{max}$ 242 nm ($\epsilon$ 3312). $^1$H n.m.r. $\delta$ (CDCl$_3$) 0.90, t, J 7.2 Hz, 3H, CH$_3$; 1.32, m 8H, CH$_2$; 1.86, m, 2H, CH$_2$; 2.50, m, 2H, CH$_2$; 5.93, s, 5-CHBr$_2$. $^{13}$C n.m.r. $\delta$ (CDCl$_3$): 13.9, CH$_3$; 22.5, 26.5, 28.2, 28.6, 29.8, 31.5, CH$_2$; 43.4, 5-CHBr$_2$; 94.0, C5; 112.6, C3; 163.3, C4; 164.4, C2.

5-(Bromomethyl)-5-bromo-4-phenyl-2(5H)-furanone

Colourless prisms (79%). $^1$H n.m.r. $\delta$ (CDCl$_3$) 4.11, d J, 11.3 Hz, CH$_a$Br; 4.38, d, J 11.3 Hz, CH$_b$Br. $^{13}$C n.m.r. $\delta$ (CDCl$_3$): 34.8, CH$_2$Br; 89.4, C5; 116.9, C3; 128.0, 129.2, 131.8, Ph; 165.9, C4; 167.2, C2. Mass spectrum: m/z 334 (M ($^{81}$Br$_2$), 5%); 332 (M ($^{81}$Br), ($^{79}$Br), 10%); 330 (M ($^{79}$Br$_2$), 4%); 253 (10); 251 (10); 172 (40); 116 (50); 115 (50); 102 (100).

General Methods for the Synthesis of Halogenated 5-(Halomethylene)-2(5H)-Furanones Examples of the preparation of 3-bromo-4-alkyl-5-(bromomethylene)-2(5H)-furanone produced are provided below.

General Method F:—for the synthesis of 3-bromo-4-alkyl-5-(bromomethylene)-2(5H)-furanone A solution of N,N'-diisopropylethyl amine (Hunig's base) (36 mmol) in dichloromethane (10 ml) was added dropwise with stirring to an ice cooled solution of 3,5-dibromo-5-bromomethyl-4-alkyl-2(5H)-furanone (7.2 mmol) in dichloromethane (40 ml). The mixture was allowed to warm to room temperature and further stirred at room temperature for 60 h. The resulting mixture was washed with aqueous hydrochloric acid (100 ml, 2 M), dried over anhydrous sodium sulfate and evaporated to yield 3-bromo-4-alkyl-5-(bromomethylene)-2(5H)-furanone as a dark brown oil. The crude product was chromatographed on a silica gel column using dichloromethane/light petroleum (60–80° C.) (1:3) as eluent to yield the pure furanone as a pale yellow oil.

3-Bromo-4-methyl-5-bromomethylene)-2(5H)-furanone

Pale yellow oil (64%). $v_{max}$ 2905, 2850, 1760, 1630, 1580, 1450, 1380, 1270, 1230, 1105, 980, 900, 720 cm$^{-1}$. $\lambda_{max}$ 290 nm ($\epsilon$ 20570). $^1$H n.m.r. $\delta$ (CDCl$_3$) 2.16, s, 3H, CH$_3$; 6.22, s, 5-(CHBr). $^{13}$C n.m.r. $\delta$ (CDCl$_3$): 11.5, CH$_3$; 90.4, 5-(CHBr); 112.2, C3; 149.3, C5; 152.0, C4; 163.4, C2. Mass spectrum: m/z 270 (M ($^{81}$Br$_2$), 40%); 268 (M ($^{81}$Br, $^{79}$Br), 80); 266 (M, ($^{81}$Br$_2$), 40%); 242 (5); 240 (10); 238 (10); 189 (10); 187 (10); 161 (12); 159 (12); 133 (20); 131 (20); 122 (15); 120 (15).

3-Bromo-5-(dibromomethylene)-4-methyl-2(5H)-furanone

Colourless prisms (9%). $v_{max}$ 2951, 2924, 2853, 1771, 1592, 1576, 1462, 1428, 1382, 1232, 1020, 906, 847, 746, 718 cm$^{-1}$. $\lambda_{max}$ 307 nm ($\epsilon$ 24576). $^1$H n.m.r. $\delta$ (CDCl$_3$) 2.50, s, 3H, CH$_3$. $^{13}$C n.m.r. $\delta$ (CDCl$_3$): 16.4, CH$_3$; 81.6, 5-(CBr$_2$); 115.9, C3; 148.8, C5; 149.5, C4; 162.2, C2. Mass spectrum: m/z 350 (M ($^{81}$Br$_3$), 30%); 348 (M ($^{81}$Br$_2$) ($^{79}$Br), 100%); 346 (M ($^{81}$Br) ($^{79}$Br$_2$), 100%); 344 (M ($^{79}$Br$_3$), 30%); 269 (10); 267 (20); 265 (10); 241 (10); 239 (20); 237 (10); 213 (20); 211 (40); 209 (20); 202 (10); 200 (20); 198 (10).

3-Bromo-5-(bromomethylene)-4-propyl-2(5H)-furanone

Pale yellow oil (58%). $v_{max}$ 2936, 2843, 1760, 1595, 1440, 1380, 1270, 1190, 1100, 1010, 950, 845, 760, 710 cm$^{-1}$. $\lambda_{max}$ 287 nm ($\epsilon$ 13757). $^1$H n.m.r. δ (CDCl$_3$) 1.01, t, J 7.5 Hz, 3H, CH$_3$; 1.67, m, 2H, CH$_2$; 2.52, t, J 7.2 Hz, t, 2H, CH$_2$; 6.23, s, 5-(CHBr). $^{13}$C n.m.r. δ (CDCl$_3$): 13.9, CH$_3$; 21.8, 28.0, CH$_2$; 90.8, 5-(CHBr); 112.0, C3; 151.5, C5; 153.3, C4; 163.6, C2. Mass spectrum: m/z 298 (M ($^{81}$Br$_2$), 20%); 296 (M ($^{81}$Br, $^{79}$Br), 40); 294 (M, ($^{81}$Br$_2$), 20%); 217 (100); 215 (100%); 189 (60); 187 (60); 159 (20); 161 (20); 136 (100).

3-Bromo-4-butyl-5-(bromomethylene)-2(5H)-furanone

Pale yellow oil (52%). $\nu_{max}$ 2950, 2850, 1750, 1590, 1450, 1380, 1310, 1270, 1195, 1100, 1050, 1010, 950, 890, 840, 760, 720 cm$^{-1}$. $\lambda_{max}$ 295 nm ($\epsilon$ 9827). $^1$H n.m.r. δ (CDCl$_3$) 0.96, t, J 7.2 Hz, 3H, CH$_3$; 1.42, m, 2H, CH$_2$; 1.57, m, 2H, CH$_2$; 2.53, t, J 7.5 Hz, t, 2H, CH$_2$; 6.23, s, 5-(CHBr). $^{13}$C n.m.r. δ (CDCl$_3$): 13.5, CH$_3$; 22.6, 25.8, 30.3, CH$_2$; 90.7, 5-(CHBr); 111.6, C3; 151.3, C5; 153.5, C4; 163.6, C2. Mass spectrum: m/z 312 (M ($^{81}$Br$_2$), 8%); 310 (M ($^{81}$Br, $^{79}$Br), 16); 306 (M ($^{81}$Br$_2$), 8%); 270 (20); 268 (40); 266 (20); 231 (20), 229 (20); 217 (15); 215 (15); 189 (60); 187 (60); 159 (20); 161 (20).

3-Bromo-5-(dibromomethylene)-4-butyl-2(5H)-furanone

Pale yellow needles (10%). $\nu_{max}$ 2980, 2952, 2850, 1766, 1615, 1575, 1462, 1380, 1150, 1009, 910, 830, 760, 720cm$^{-1}$. $\lambda_{max}$ 310 nm ($\epsilon$ 2350). $^1$H n.m.r. δ (CDCl$_3$) 0.97, t, J 7.2 Hz, 3H, CH$_3$; 1.45, m, 2H, CH$_2$; 1.59, m, 2H, CH$_2$; 2.88, t, J 7.5 Hz, 2H, CH$_2$. $^{13}$C n.m.r. δ (CDCl$_3$): 13.6, CH$_3$; 22.6, 28.0, 29.9 CH$_2$; 81.2, 5-(CBr$_2$); 115.4, C3; 148.4, C5; 153.4, C4; 162.2, C2. Mass spectrum: m/z 392 (M ($^{81}$Br$_3$), 8%); 390 (M ($^{81}$Br$_2$), ($^{79}$Br), 20%); 388 (M ($^{81}$Br), ($^{79}$Br$_2$), 20%); 386 (M, ($^{79}$Br$_3$), 8%); 350 (8); 348 (20); 346 (20); 342 (8); 311 (40); 309 (100); 307 (40); 269 (40); 267 (100); 265 (40); 239 (15); 227 (20).

3-Bromo-4-hexyl-5-(bromomethylene)-2(5H)-furanone

Pale yellow oil (55%). $\nu_{max}$ 3092, 2955, 2928, 2857, 1786, 1679, 1636, 1595, 1465, 1364, 1301, 1219, 1183, 1050, 982, 914, 840, 765, 750 cm$^{-1}$. $\lambda_{max}$ 290 nm ($\epsilon$ 5647). $^1$H n.m.r. δ (CDCl$_3$) 0.90, t, J 7.2 Hz, 3H, CH$_3$; 1.33, m, 6H, CH$_2$; 1.61, m, 2H, CH$_2$; 2.52, t, J 7.9 Hz, t, 2H, CH$_2$; 6.22, s, 5-(CHBr). $^{13}$C n.m.r. δ (CDCl$_3$): 13.9, CH$_3$; 22.3, 26.1, 28.2, 29.0, 31.2, CH$_2$; 90.5, 5-(CHBr); 111.7, C3; 151.4, C5; 153.5, C4; 163.5, C2. Mass spectrum: m/z 340 (M ($^{81}$Br$_2$), 20%); 338 (M ($^{81}$Br, $^{79}$Br), 40); 336 (M, ($^{81}$Br$_2$), 20%); 270 (20); 268 (40); 266 (20); 259 (44), 257 (44); 215 (30); 213 (30); 189 (100); 187 (100); 178 (30); 176 (30); 159 930); 149 (40); 135 (70); 121 (80).

3-Bromo-4-heptyl-5-(bromomethylene)-2(5H)-furanone

Pale yellow oil (60%). $\nu_{max}$ 3094, 2953, 2928, 2856, 1789, 1636, 1596, 1464, 1377, 1268, 1183, 1046, 981, 891, 840, 764, 749 cm$^{-1}$. $\lambda_{max}$ 293 nm ($\epsilon$ 14610). $^1$H n.m.r. δ (CDCl$_3$) 0.89, t, J 7.2 Hz, 3H, CH$_3$; 1.33, m, 8H, CH$_2$; 1.59, m, 2H, CH$_2$; 2.52, t, J 7.5 Hz, t, 2H, CH$_2$; 6.22, s, 5-(CHBr). $^{13}$C n.m.r. δ (CDCl$_3$): 13.9, CH$_3$; 22.5, 26.1, 28.2, 28.7, 29.3, 31.5, CH$_2$; 90.5, 5-(CHBr); 111.6, C3; 151.4, C5; 153.5, C4; 163.5, C2. Mass spectrum: m/z 354 (M ($^{81}$Br$_2$), 15%); 352 (M ($^{81}$Br, $^{79}$Br), 30); 350 (M, ($^{81}$Br$_2$), 15%); 270 (25); 268(50); 266 (25); 231 (40); 257 (44); 215 (30); 213 (30); 189 (100); 187 (100); 173 (100); 145 (40); 135 (20); 121 (40).

3-Bromo-4-decyl-5-(bromomethylene)-2(5H)-furanone

Pale yellow oil (28%). $\nu_{max}$ 2925, 2850, 1789, 1636, 1590, 1450, 1380, 1100, 980, 890, 750, 720 cm$^{-1}$. $^1$H n.m.r. δ (CDCl$_3$) 0.89, t J 7.0 Hz, 3H, CH$_3$; 1.32, m, 14H, CH$_2$; 1.58, m, 2H, CH$_2$; 2.52, t J 7.5 Hz, t, 2H, CH$_2$; 6.23, s, 5-(CHBr). $^{13}$C n.m.r. δ (CDCl$_3$): 14.0, CH$_3$; 22.5, 26.1, 28.2, 29.0, 29.1, 29.3, 29.4, 31.7, CH$_2$; 90.7, 5-(CHBr); 111.6, C3; 151.3, C5; 153.6, C4; 163.5, C2. Mass spectrum: m/z 396 (M ($^{81}$Br$_2$), 3%); 394 (M, ($^{81}$Br, $^{79}$Br), 6); 392 (M, ($^{81}$Br$_2$), 3%); 315 (10); 313 (10); 270 (5); 268 (10); 266 (5); 257 (44); 231 (10), 215 (30); 189 (20); 187 (20).

3-Bromo-4-methyl-5-(ethylidene)-2(5H)-furanone

Pale yellow solid (42%). $\nu_{max}$ 2952, 2850, 1778, 1630, 1430, 1380, 1270, 1238, 1105, 1047, 912, 854, 720 cm$^{-1}$. $^1$H n.m.r. δ (CDCl$_3$) 1.93, d, J 7.2 Hz, 3H, CH$_3$; 2.12, s, 3H, CH$_3$; 5.47, q, J 7.2 Hz, 5-(CHMe). $^{13}$C n.m.r. δ (CDCl$_3$): 11.5, CH$_3$; 11.6, CH$_3$; 109.2, 5-(CHMe); 110.0, C3; 149.9, C5; 150.8, C4; 165.0, C2. Mass spectrum: m/z 204 (M ($^{81}$Br), 5%); 202 (M, ($^{79}$Br), 5%); 192 (10); 190 (10); 178 (20); 176 (20); 148 (10); 146 (10).

General Methods for the Synthesis of 4-alkyl-, and 4-Bromo-5-(Halomethylene)-2(5H)-Furanones Examples of the preparation of 4-alkyl-5-(bromomethylene)- and 4-bromo-5-(bromomethylene)-2(5H)-furanone are provided below.

Synthesis of 4-alkyl-5-(bromomethylene)- and 4-bromo-5-(bromomethylene)-2(5H)-furanone General Method G:

Synthesis of 4-alkyl-5-(bromomethylene)-2(5H)-furanones 2,3-Dibromo-3-alkyl-4-oxopentanoic acid (5 g) was added with stirring to hot concentrated sulfuric acid (30 ml) held at 100° C. The mixture was further heated with stirring at this temperature for 20 minutes, cooled to ambient temperature and treated slowly with ice water. The resulting oily product was extracted with dichloromethane (3×75 ml). The combined extracts were washed with saturated sodium bicarbonate solution, dried over anhydrous sodium sulfate and evaporated to yield the 4-alkyl-5-(bromomethylene)-2(5H)-furanone as a pale yellow oil. The crude product was chromatographed on a silica gel column using dichloromethane/light petroleum (1:1) as eluent to yield pure 4-alkyl-5-(bromomethylene)-2(5H)-furanone (50–60%) as a pale yellow oil. Further elution of the column with dichloromethane yielded 4-alkyl-5-bromo-5-bromomethyl-, 4-alkyl-5-bromo-5-dibromomethyl- and 4-alkyl-5-(dibromomethylene)-2(5H)-furanones (5–8%).

General Method H:

3-alkyl-4-oxo-2-pentenoic acid (7.8 mmol) was added with stirring to hot concentrated sulfuric acid (10 ml) held at 100° C. The mixture was further heated with stirring at this temperature for 10 minutes, cooled to ambient temperature and treated slowly with bromine (11.7 mmol). The mixture was stirred at room temperature for 15 minutes and then at 100° C. for further 15 minutes. The mixture was cooled to room temperature and poured over crushed ice. The resulting oily product was extracted with dichloromethane (3×50 ml). The combined extract was washed with saturated sodium bicarbonate solution, dried over anhydrous sodium sulfate and evaporated to yield a pale yellow oil. The crude product was chromatographed on a silica gel column using dichloromethane/light petroleum (1:1) as eluent to yield 4-alkyl-5-(bromomethylene)-2(5H)-furanone (40–60%) as a pale yellow oil. Further elution of the column with dichloromethane yielded mixtures of 4-alkyl-5-bromo-5-bromomethyl-, 4-alkyl-5-bromo-5-dibromomethyl- and 4-alkyl-5-(dibromomethylene)-2(5H)-furanones (20–30%), some of which were purified.

The following 4-alkyl-5-(bromomethylene)-2(5H)-furanones were prepared according to methods G and H.

5-Bromomethylene)-4-methyl-2(5H)-furanone

Colourless prisms (52%) (Found: (HRESMS) m/z 210.9370. C$_6$H$_5$BrO$_2$Na ($^{79}$Br) requires m/z 210.9365). $\nu_{max}$ 2920, 2850, 1765, 1590, 1460, 1380, 1230, 1020, 910, 850, 750, 720 cm$^{-1}$. $\lambda_{max}$ 281 nm ($\epsilon$ 20675). $^1$H n.m.r. δ (CDCl$_3$) 2.11, d J 1.3 Hz, 3H, CH$_3$; 5.98, q J 1.3 Hz, H3; 6.02, s, 5-(CHBr). $^{13}$C n.m.r. δ (CDCl$_3$): 12.1, CH$_3$; 89.8, 5-(CHBr);

117.9, C3; 153.6, C5; 154.0, C4; 168.0, C2. High resolution mass: observed 210.9370 C6H5BrO2Na requires: Mass spectrum: m/z 190 (M ($^{81}$Br), 90%); 188 (M, ($^{79}$Br), 90%); 162 (20); 160 (20); 122 (50); 120 (50).

5-Bromo-5-(dibromomethyl)-4-methyl-2(5H)-furanone

Colourless needles (22%) (Found: HRESMS) m/z 368.7749. C$_6$H$_5$Br$_3$O$_2$Na ($^{79}$Br) requires m/z 368.7732). $v_{max}$ 3006, 2923, 2853, 1779, 1642, 1595, 1460, 1380, 1330, 1290, 1182, 1140, 1085, 911, 868, 750, 720 cm$^{-1}$. $\lambda_{max}$ 212 nm (ε 8401). $^1$H n.m.r. δ (CDCl$_3$) 2.28, d J 1.5 Hz, 3H, CH$_3$; 5.89 s, 5-(CHBr$_2$), 6.10, q J 1.5 Hz, H3. $^{13}$C n.m.r. δ (CDCl$_3$): 13.5, CH$_3$; 43.1, 5-(CHBr$_2$); 94.5, C5; 118.5, C3; 166.6, C4; 166.9, C2. Mass spectrum: m/z 352 (M ($^{81}$Br$_3$), 3%); 350 (M ($^{81}$Br$_2$)($^{79}$Br), 6%); 348 (M ($^{81}$Br) ($^{79}$Br$_2$), 6%); 346 (M ($^{79}$Br$_3$), 3%); 269 (15); 267 (30); 265 (15); 241 (15); 239 (30); 237 915); 213 (20); 211 (40); 209 (20); 202 (12); 204 (24); 206 (12).

5-(Bromomethylene)-4-propyl-2(5H)-furanone

Pale yellow oil (48%). $v_{max}$ 3080, 2950, 2850, 1780, 1630, 1595, 1460, 1380, 1330, 1290, 1150, 1085, 1020, 920, 830, 750, 720 cm$^{-1}$. $^1$H n.m.r. δ (CDCl$_3$) 0.90, t, J 7.5 Hz, 3H, CH$_3$; 1.65, m, 2H, CH$_2$; 2.44, t, J 7.5 Hz, 2H, CH$_2$; 6.03, s, H3; 6.10, s, 5-(CHBr). $^{13}$C n.m.r. δ (CDCl$_3$): 13.5, CH$_3$; 21.2, 27.9, CH$_2$; 89.2, 5-(CHBr); 116.2, C3; 153.0, C5; 157.7, C4; 167.7, C2. Mass spectrum: m/z 218 (M ($^{81}$Br), 40%); 216 (M, ($^{79}$Br), 40%); 203 (20); 201 (20); 190 (25); 188 (25); 137 (100); 122 (50); 118 (50); 109 (70).

5-(Dibromomethylene)-4-propyl-2(5H)-furanone

Colourless prisms (12%). $v_{max}$ 3070, 2950, 2850, 1775, 1630, 1590, 1460, 1380, 1150, 1090, 1020, 920, 830, 760 cm$^{-1}$. $^1$H n.m.r. δ (CDCl$_3$) 1.04, t, J 7.2 Hz, 3H, CH$_3$; 1.70, m, 2H, CH$_2$; 2.77, t, J 8.4 Hz, 2H, CH$_2$; 6.18, t, J 1.5 Hz, H3. $^{13}$C n.m.r. δ (CDCl$_3$): 13.6, CH$_3$; 21.2, 31.7, CH$_2$; 80.2, 5-(CHCl$_3$); 119.4, C3; 149.8, C5; 158.2, C4; 165.9, C2. Mass spectrum: m/z 298 (M ($^{81}$Br$_2$), 25%); 296 (M ($^{81}$Br), ($^{79}$Br) 50%); 294 (M ($^{79}$Br$_2$), 25%); 283 (10); 281 (20); 279 (10); 268 (40); 254 (25); 217 (100); 215 (100); 202 (30); 200 (60); 198 (30); 189 (25); 187 (25); 174 (10); 172 (20); 170 (10).

5-(Bromomethylene)-4-butyl-2(5H)-furanone

Pale yellow oil (56%). $v_{max}$ 2995, 2950, 2850, 1780, 1610, 1595, 1460, 1380, 1350, 1290, 1150, 1090, 1020, 920, 840, 750, 720 cm$^{-1}$. $\lambda_{max}$ 281 nm (ε 10540). $^1$H n.m.r. δ (CDCl$_3$) 0.90, t, J 7.5 Hz, 3H, CH$_3$; 1.41, m, 2H, CH$_2$; 1.62, m, 2H, CH$_2$; 2.42, t, J 8.2 Hz, 2H, CH$_2$; 6.02, s, H3; 6.10, s, 5-(CHBr). $^{13}$C n.m.r. δ (CDCl$_3$): 13.9, CH$_3$; 22.4, 25.9, 27.7, 28.7, 31.3, CH$_2$; 89.3, 5-(CHBr); 116.1, C3; 152.9, C5; 158.1, C4; 167.8, C2. Mass spectrum: m/z 232 (M ($^{81}$Br), 20%); 230 (M, ($^{79}$Br), 20%); 203 (10); 201 (10); 190 (60); 189 (60); 151 (75); 123 (40); 109 (100).

5-(Bromomethylene)-4-hexyl-2(5H)-furanone

Pale yellow oil (63%). $v_{max}$ 3095, 2930, 2850, 1778, 1638, 1600, 1450, 1160, 1028, 920, 758 cm$^{-1}$. $\lambda_{max}$ 283 nm (ε 5093). $^1$H n.m.r. δ (CDCl$_3$) 0.90, t, J 7.1 Hz, 3H, CH$_3$; 1.32, m, 8H, CH2; 1.62, m, 2H, CH$_2$; 2.42, t, J 6.8 Hz, 2H, CH$_2$; 6.02, s, H3; 6.09, s, 5-(CHBr). $^{13}$C n.m.r. δ (CDCl$_3$): 13.6, CH$_3$; 22.3, 25.7, 29.9, CH$_2$; 89.4, 5-(CHBr); 116.1, C3; 153.0, C5; 158.3, C4; 167.8, C2. Mass spectrum: m/z 260 (M ($^{81}$Br), 10%); 258 (M, ($^{79}$Br), 10%); 190 (40); 188 (40); 179 (50); 151 (30); 137 (40); 109 (60).

5-Bromo-5-(Bromomethyl)-4-hexyl-2(5H)-furanone

Pale yellow oil (14%). $v_{max}$ 3111, 3039, 2954, 2929, 2854, 1793, 1637, 1600, 1465, 1414, 1377, 1263, 1237, 1178, 1151, 1124, 992, 910, 858 cm$^{-1}$. $\lambda_{max}$ 214 nm (ε 1054). $^1$H n.m.r. δ (CDCl$_3$) 0.91, t, J 7.1 Hz, 3H, CH$_3$; 1.35, m, 4H, CH$_2$; 1.47, m, 2H, CH$_2$; 1.71, m, 2H, CH$_2$; 2.51, m, 2H, CH$_2$; 3.94, d, J 11.7 Hz, CH$_a$Br; 4.26, d, J 11.7 Hz, CH$_b$Br; 6.03, bs, H3. $^{13}$C n.m.r. δ (CDCl$_3$): 13.9, CH$_3$; 22.4, 26.2, 26.8, 28.6, 31.3, CH$_2$; 33.8, 5-(CH$_2$Br); 91.8, C5; 116.8, C3; 167.8, C4; 171.3, C2. Mass spectrum: m/z 342 (M ($^{81}$Br$_2$), 3%); 340 (M ($^{81}$Br), ($^{79}$Br), 3%); 338 (M, ($^{79}$Br$_2$), 3%); 325(5), 314 (5); 261 (8); 259 (8); 191 (10); 189 (10); 152 915); 137 (30); 110 (60).

5-(Bromomethylene)-4-heptyl-2-(5H)-furanone

Pale yellow oil (61%). $v_{max}$ 3095, 2920, 2850, 1770, 1630, 1595, 1450, 1360, 1280, 1150, 1100, 1020, 910, 840, 750, 720 cm$^{-1}$. $\lambda_{max}$ 214 nm (ε 9590). $^1$H n.m.r. δ (CDCl$_3$) 0.89, t, J 7.1 Hz, 3H, CH$_3$; 1.32, m, 10H, CH$_2$; 1.62, m, 2H, CH$_2$; 2.44, t, J 8.4 Hz, 2H, CH$_2$; 6.01, s H3; 6.09, s, 5-(CHBr). $^{13}$C n.m.r. δ (CDCl$_3$): 13.9, CH$_3$; 22.5, 25.9, 27.8, 28.7, 29.0, 31.5, CH$_2$; 89.2, 5-(CHBr); 116.1, C3; 153.0, C5; 158.1, C4; 167.7, C2. Mass spectrum: m/z 274 (M ($^{81}$Br), 10%); 272 (M, ($^{79}$Br), 10%); 193 (100); 190 (75); 188 (75); 165 (70); 151 (80); 123 (60); 109 (100).

5-(Dibromomethylene)-4-heptyl-2(5H)-furanone

Pale yellow solid (6%). $v_{max}$ 3085, 2925, 2850, 1759, 1586, 1463, 1360, 1280, 1175, 1068, 959, 836, 720 cm$^{-1}$. $\lambda_{max}$ 296 nm (ε 8857). $^1$H n.m.r. δ (CDCl$_3$) 0.89, t, J 7.1 Hz, 3H, CH$_3$; 1.36, m, 10H, CH$_2$; 1.66, m, 2H, CH$_2$; 2.76, t, J 7.0 Hz, 2H, CH$_2$; 6.17, t, J 1.5 Hz, H3. $^{13}$C n.m.r. δ (CDCl$_3$): 13.9, CH$_3$; 22.5, 27.8, 28.8, 29.0, 29.8, 31.5, CH$_2$; 80.2, 5-(CBr$_2$); 119.3, C3; 149.8, C5; 158.5, C4; 166.0, C2. Mass spectrum: m/z 354 (M ($^{81}$Br$_2$), 5%); 352 (M ($^{81}$Br, $^{79}$Br), 10); 350 (M, ($^{79}$Br$_2$), 15%); 273 (80); 270 (15); 268 (30); 266 (15); 240 (8); 211 (20); 200 (10); 189 (15); 187 (15).

5-Bromo-5-(bromomethyl)-4-heptyl-2(5H)-furanone

Pale yellow oil (14%). $v_{max}$ 3111, 3039, 2954, 2929, 2856, 1794, 1638, 1465, 1416, 1378, 1264, 1237, 1178, 1152, 1124, 990, 910, 858, 710 cm$^{-1}$. $\lambda_{296}$ nm (ε 8857). $^1$H n.m.r. δ (CDCl$_3$) 0.91, t, J 7.1 Hz, 3H, CH$_3$; 1.31–1.45, m, 8H, CH$_2$; 1.73, m, 2H, CH$_2$; 2.32, m, 1H, CH$_2$; 2.53, m, 1H, CH$_2$; 3.93, d, J 11.7 Hz, CH$_a$Br; 4.26, d, J 11.7 Hz, CH$_b$Br; 6.03, bs, H3. $^{13}$C n.m.r. δ (CDCl$_3$): 13.9, CH$_3$; 22.5, 26.2, 26.8, 28.8, 28.9, 31.5, CH$_2$; 33.8, 5-CH$_2$Br); 91.7, C5; 116.8, C3; 167.8, C4; 171.2, C2. Mass spectrum: m/z 356 (M ($^{81}$Br$_2$), 3%); 354 (M ($^{81}$Br), ($^{79}$Br), 3%); 352 (M, ($^{79}$Br$_2$), 3%); 311 (5), 314 (5); 281 (8); 250 (8); 232 (5); 194 (10); 189 (10); 166 (5); 151 (15); 137 (30); 110 (60).

5-(Bromomethylene)-4-decyl-2(5H)-furanone

Pale yellow oil (22%). $v_{max}$ 3118, 3088, 2923, 2852, 1781, 1761, 1602, 1465, 1160, 1100, 923, 890, 760 cm$^{-1}$. $^1$H n.m.r. δ (CDCl$_3$) 0.88, t, J 7.2 Hz, 3H, CH$_3$; 1.32, m, 14H, CH$_2$; 1.62, m, 2H, CH$_2$; 2.44, t, J 8.2 Hz, 2H, CH$_2$; 6.02, s, H3; 6.09, s, 5-(CHBr). $^{13}$C n.m.r. δ (CDCl$_3$): 14.1, CH$_3$; 22.7, 26.0, 27.9, 29.2, 29.2, 29.3, 29.4, 29.5, 31.9, CH$_2$; 89.3, 5-(CHBr); 111.6, C3; 153.1, C5; 158.2, C4; 167.8, C2. Mass spectrum: m/z 316 M ($^{81}$Br), 5%); 314 (M, ($^{79}$Br), 5%); 282 (5); 267 (5); 253 (5); 235 (10); 217 (5); 207 (10); 190 (10); 188 (10); 175 (5); 165 910); 151 (10); 133 (15); 123 915); 109 920).

5-(Bromomethylene)-4-phenyl-2(5H)-furanone

Colourless prisms (52%). $v_{max}$ 3090, 2920, 2850, 1760, 1630, 1605, 1590, 1440, 1385, 1340, 1260, 1160, 1080, 950, 900, 840, 760, 710 cm$^{-1}$. $\lambda_{max}$ 251 nm (ε 2263). $^1$H n.m.r. δ (CDCl$_3$) 6.25, s, 5-(CHBr); 6.30, s, H3. $^{13}$C n.m.r. δ (CDCl$_3$): 93.1, 5-(CHBr); 116.1, C3; 128.2, 129.2, 130.9, Ph; 151.8, C5; 155.7, C4; 167.0, C2. Mass spectrum: m/z 252 (M ($^l$Br), 10%); 250 (M, ($^{79}$Br), 10%); 172 (30); 144 (10); 116 (50); 114 (50); 102 (100).

Synthesis of 4-bromo-5-(bromomethylene)-2(5H)-furanone (i) Crude 2,3,5-tribromo-4-oxopentanoic acid (1.0 g) was treated according to method G to yield 4-bromo-5-bromomethylene-2(5H)-furanone (0.6 g, 83%) as colourless needles m.p. 97–98° C. $v_{max}$ 3160, 3120, 1805, 1783, 1644, 1565, 1314, 1244, 1156, 1101, 976, 892, 831 cm$^{-1}$. $\lambda_{max}$ 290 nm ($\epsilon$ 8230). $^1$H n.m.r. δ (CDCl$_3$) 6.42, s, 5-CHBr; 6.50, s, H3. $^{13}$C n.m.r. δ (CDCl$_3$): 93.8, 5-CHBr; 121.0, C3; 135.3, C4; 151.5, C5; 165.5, C2.

(ii) 2,3-Dibromo-4-oxopentanoic acid (1 g) was treated according to method G to yield 4-bromo-5-bromomethylene-2(5H)-furanone (0.4 g, 50%) as colourless needles m.p. 97–98° C.

General Methods for the Synthesis of 4-(1'-Haloalkyl)-5-(Halomethylene)-, and 3-Bromo-4-(1'-Haloalkyl)-5-(Halomethylene)-2-(5H)-Furanones An example of 3-bromo-4-(1-bromoalkyl)-5-halomethylene)-2(5H)-furanone produced is provided below.

General Method I:—for the synthesis of 3-bromo-4-(1-bromoalkyl)-5-(halomethylene)-, and 4-(1-bromoalkyl)-5-(halomethylene)-2(5H)-furanone N-Halosuccinimide (2.43 mmol) was added to a solution of 3-bromo-4-alkyl-5-(halomethylene)-, or 4-alkyl-5-(halomethylene)-2(5H)-furanone (2.43 mmol) in carbon tetrachloride (15 ml) containing a few crystals of benzoyl peroxide. The mixture was irradiated with a 250 W lamp and refluxed in an oil bath for 18 h. After cooling the mixture to room temperature it was filtered and the precipitate washed with carbon tetrachloride (50 ml). The combined filtrate and washings were evaporated under reduced pressure and the crude product was purified by silica gel chromatography using dichloromethane/light petroleum (1:2) as the eluent to yield the 1-haloalkyl compounds (45–55%).

3-Bromo-4-(1'-bromoheptyl)-5-(bromomethylene)-2(5H)-furanone

Colourless oil (52%). $v_{max}$ 3101, 2954, 2927, 2866, 1790, 1632, 1585, 1463, 1377, 1270, 1177, 992, 897, 774, 748 cm$^{-1}$. $\lambda_{max}$ 305 nm ($\epsilon$ 11284). $^1$H n.m.r. δ (CDCl$_3$) 0.88, t, J 7.2 Hz, 3H, CH$_3$; 1.29, m, 6H, CH$_2$; 1.48, m, 2H, CH$_2$; 2.25, m, 2H, CH$_2$; 4.87, t, J 7.9 Hz, 2H, CH$_2$; 6.65, s, 5-(CHBr). $^{13}$C n.m.r. δ (CDCl$_3$): 13.9, CH$_3$; 22.3, 27.7, 28.2, 31.3, 37.7, 40.4, CH$_2$; 93.5, 5-(CHBr); 112.6, C3; 148.5, C5; 150.6, C4; 162.3, C2. Mass spectrum: m/z 434 (M ($^{81}$Br$_3$), 3%); 432 (M ($^{81}$Br$_2$)($^{79}$Br), 6%); 430 (M ($^{81}$Br) ($^{79}$Br$_2$), 6%); 428 (M ($^{79}$Br$_3$), 3%); 408 (10); 391 (10); 354 (20); 352 (35); 350 (20); 328 (10); 326 (10); 270 (60); 268 (100); 266 (60); 229 (10); 213 915); 189 (30); 173 (30).

Figure 2:
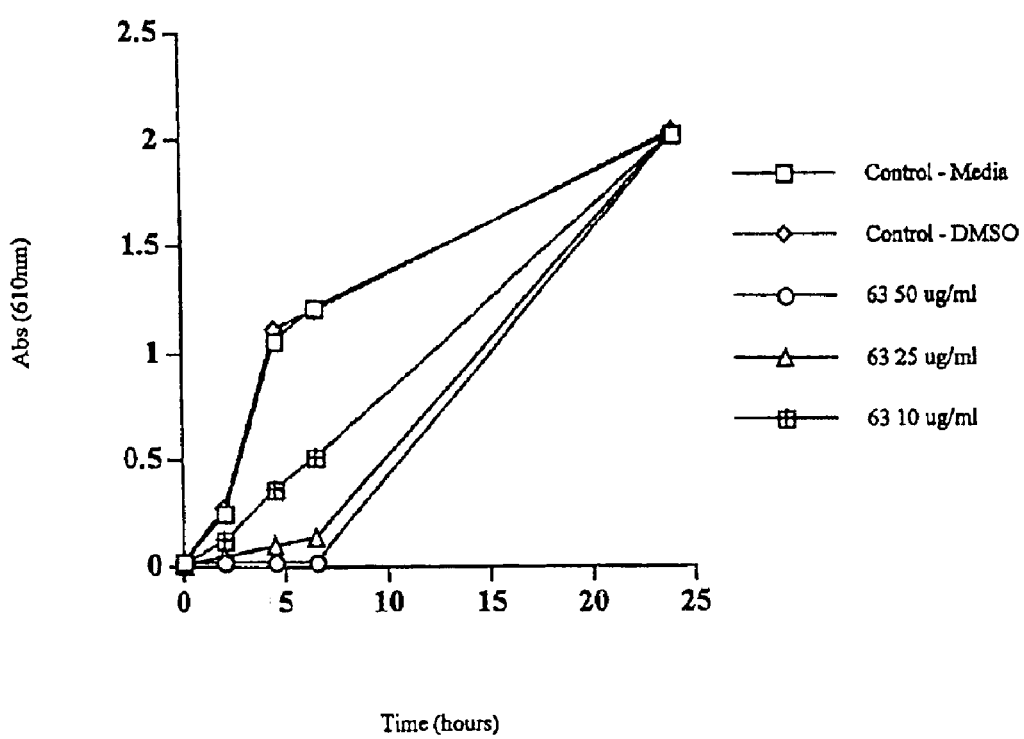
FIG. 2 is a graph showing growth of *Staphylococcus aureus* against compound 63.
Figure 3:
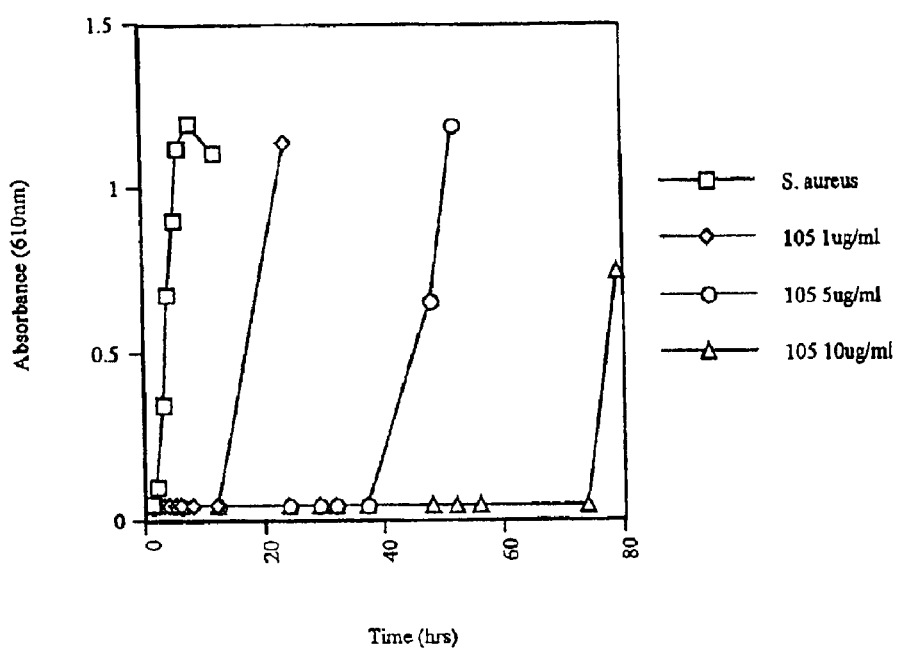
FIG. 3 is a graph showing growth of *Staphylococcus aureus* against compound 105.
Figure 4:
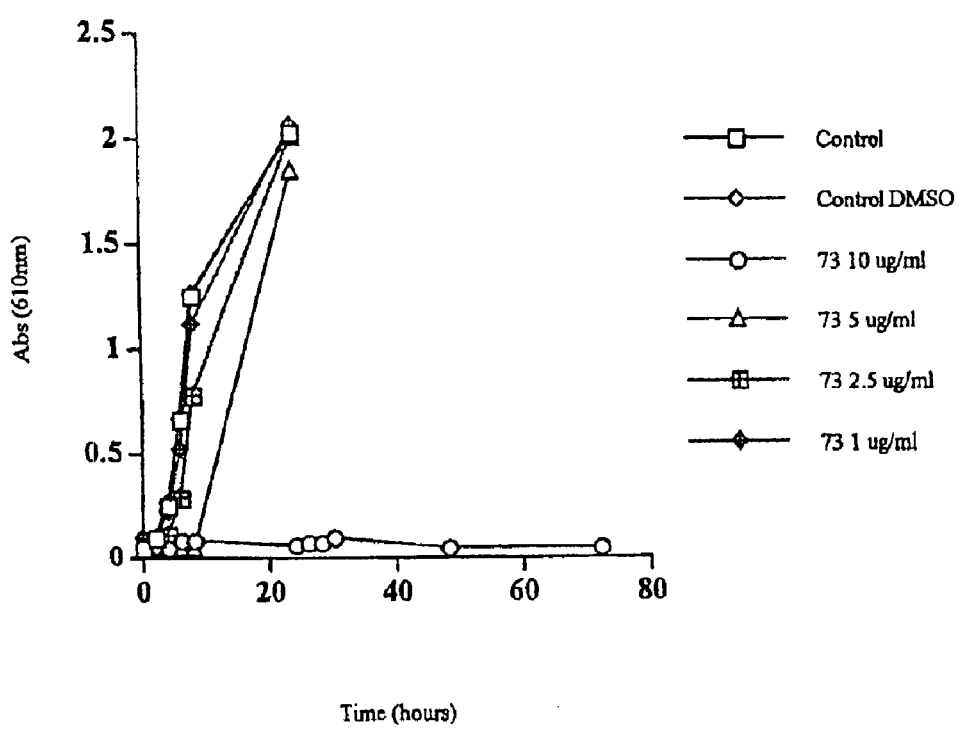
FIG. 4 is a graph showing growth of *Candida albicans* against compound 73.
Figure 5:
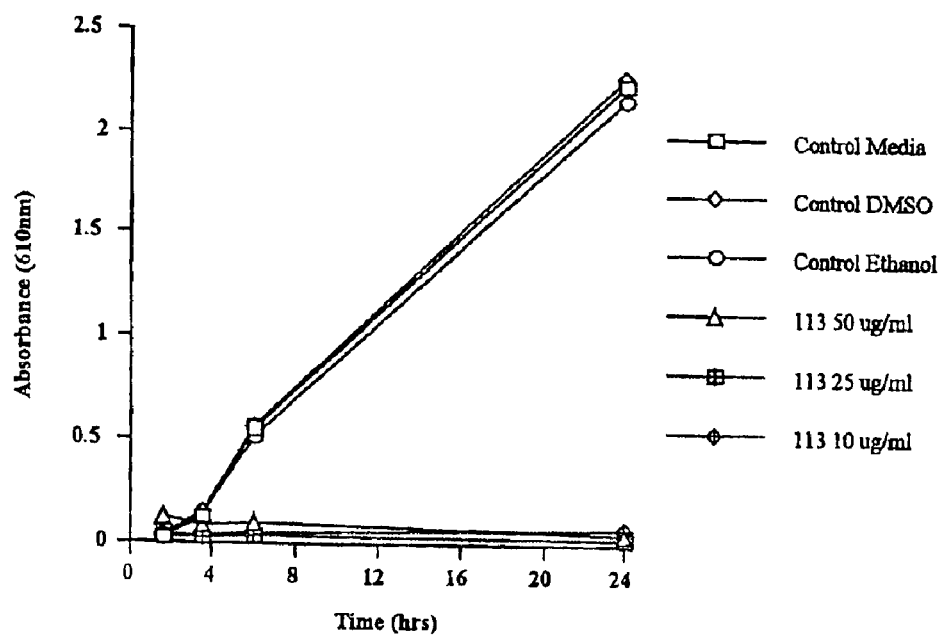
FIG. 5 is a graph showing Growth of *Candida albicans* against compound 113.

Biological Activity of Furanones
Growth of *Staphylococcus aureus* and *Candida albicans* against Furanones (FIGS. 1–5)
Material and Methods The growth of *Staphylococcus aureus* against furanones was tested in sidearm flasks. One percent of an overnight culture was added to the growth media, Nutrient Broth, containing furanones at the concentrations 1–50 μg/ml. The bacteria were incubated at 37 C and growth was measured at 610 nm.

Results

The results demonstrated that furanone 63 prolonged the lag phase of growth at 25 and 50 μg/ml. The effect of prolonged lag phase of growth was also demonstrated with compound 105. Ten μg/ml inhibited the growth of *S. aureus* for 72 hrs. No growth was detected with compound 120 at 1 μg/ml.

*Candida albicans* were grown in Sabouraud dextrose media at 37 C. One percent of overnight culture was inoculated to 10 ml of growth media containing furanones at concentrations 1–50 μg/ml. The growth was measured at 610 nm for 72 hrs for compound 73 and 24 hrs for compound 113. Ten μg/ml of compound 73 completely inhibited the growth of *C. albicans* while 5 μg/ml gave a prolonged lag phase of 8 hrs. Compound 113 completely inhibited the growth for at least 24 hrs at 10 μg/ml.

Effect of Furanones as Inhibitor of AHL-mediated Quorum Sensing, Attachment/Biofilm Formation, Two-component Signal Transduction Assay and AI-2 Activity
Methods
Gfp Assay Briefly, the Gfp assay determines the relative effectiveness of a compound as an inhibitor of AHL mediated quorum sensing. The assay is dependent on a bacterial strain that carries a reporter plasmid. This plasmid expresses the green fluorescent protein (Gfp) in the presence of AHLs (2). The presence of a competitor will prevent AHL mediated Gfp expression of the reporter. The assay can be used to generate an index of inhibition for each compound. The results here, presented as good, moderate, or poor, are based on the index of each of the compounds as an inhibitor of AHL mediated quorum sensing using this bioassay.

Attachment/Biofilm Formation

The ability of furanones to inhibit biofilm formation or attachment has been determined using a modification of the 96 well microtitre method described by Christensen et al. ((1)). The furanones are added to the wells of the microplate and the solvent is allowed to evaporate, leaving the furanones adsorbed onto the plate. Then a suspension of the monitor bacterium, *Pseudomonas aeruginosa*, is added to each well and incubated for 24 h. Following incubation, the wells are rinsed to remove unattached or loosely adhered cells. The attached wells are fixed with formaldehyde and subsequently stained with crystal violet. Following extensive washing to remove the crystal violet, the wells are read at 600 nm. The attachment/biofilm formation in the presence of the furanones is calculated as the percentage of the controls, which are not exposed to the furanones.

Two-Component Signal Transduction Assays
Taz-1 Assay

The Taz-assay carried out according to the method of Jin and Inouye (1993) with the following alterations. *E. coli* RU1012 (pYT0301) were grown overnight in M9 medium at 37° C. supplemented with 100 ug/ml ampicillin and 50 ug/ml kanamycin. This overnight culture was then used to inoculate 50 ml M9 medium in side-arm flasks which were then incubated at 37° C. and shaken at 180 rpm. The OD$_{610}$ of the growing cultures was monitored regularly and when the OD$_{610}$=0.2 the cultures were placed on ice. Aspartate was added to side-arm flasks to give a final concentration of 3 mM (aspartate stock solution made up in M9 salts).

The test compound or mixtures of compounds were dissolved in ethanol and added to cultures to give the required final concentrations. Negative controls were prepared with equal volumes of ethanol. Cultures were then placed in a 37° C. incubator and shaken for 4 hours (OD$_{610}$ approximately 0.7) before being removed and put on ice. Samples were then removed for □eta-galactosidase assays carried out according to the method of Miller (1972).

*V. harveyi* Bioassay for the Detection of AI-2 Activity

The *V. harveyi* bioassay was performed as described previously (Surette and Bassler, 1998). The *V. harveyi* reporter strain BB170 was grown for 16 hours at 30° C. with shaking in AB medium. Cells were diluted 1:5,000 into 30° C. prewarmed AB medium and 90 ul of the diluted suspension was added to wells containing supernatant. Furanones were added to the wells to achieve the desired final concentrations and the final volume in each well was adjusted with sterile medium to 100 ul. Ten ul of *V. harveyi* BB152 (AI-1−, AI-2+) supernatant was used as a positive control and 10 ul of *E. coli* DH5α supernatant or sterile media was used as a negative control. This strain of *E. coli* has previously been shown to harbor a mutation in the AI-2 synthase gene, ygaG, which results in a truncated protein with no AI-2 activity (Surette et al. 1998). The microtiter plates were incubated at 30° C. with shaking at 175 rpm. Hourly determinations of the total luminescence were quantified using the chemiluminescent setting on a Wallac (Gaithersburg, Md.) model 1450 Microbeta Plus liquid scintillation counter. The *V. harveyi* cell density was monitored by the use of a microplate reader (Bio-Rad, Hercules, Calif.). Activity is reported as the percentage of activity obtained from *V. harveyi* BB152 cell-free supernatant. While the absolute values of luminescence varied considerably between experiments, the pattern of results obtained was reproducible.

The results of these experiments are summarised in the table 1.

TABLE 1

Effect of furanones as inhibitor of AHL-mediated quorum sensing, attachment/biofilm formation, two-component signal transduction assay and AI-2 activity

| AHL | 2 component | AI-2 | Biofilm/attachment (% of control) |
|---|---|---|---|
| 103 | moderate | | 100% |
| 99 | good | | |
| 105 | | increase | 81% |
| 113 | | 65% reduction | 95% |
| 72 | | 97% reduction | |
| 63 | good | 50% reduction | 90% reduction | 79% |
| 64 | good | No effect | 80% reduction | |
| 88 | | | 85% reduction | |

Christensen, G. D., W. A. Simpson, J. J. Younger, L. M. Baddour, F. F. Barrett, D. M. Melton, and E. H. Beachey. 1985. Adherence of coagulase-negative staphylococci to plastic tissue culture plates: a quantitative model for the adherence of staphylococci to medical devices. J. Clin. Microbiol. 22(6):996–1006.

Andersen, J. B., C. Sternberg, L. K. Poulsen, S. P. Bjorn, M. Givskov, and S. Molin. 1998. New unstable variants of green fluorescent protein for studies of transient gene expression in bacteria. Appl. Environ. Microbiol. 64(6) :2240–2246.

Jin, T., and M. Inouye. 1993. Ligand binding to the receptor domain regulates the ratio of kinase to phosphatase activities of the signalling domain of the hybrid *Escherichia coli* transmembrane receptor, Tazl. J. Mol. Biol. 232: 484–49

Miller, J. H. 1972. Experiments in molecular genetics. Cold Spring Harbor Laboratory, Cold Spring Harbor, N.Y.

Surette, M. G., and B. L. Bassler. 1998. Quorum sensing in *Escherichia coli* and *Salmonella typhimurium*. Proc. Natl. Acad. Sci., USA 95:7046–7050.

Surette, M. G., M. B. Miller, and B. L. Bassler. 1999. Quorum sensing in *Escherichia coli, Salmonella typhimurium*, and *Vibrio harveyi*: a new family of genes responsible for autoinducer production. Proc. Natl. Acad. Sci., USA 96:1639–1644.

Any description of prior art documents herein is not to be taken as an admission that the documents form part of the common general knowledge of the relevant art.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method for the dehydrohalogenation of a compound of formula IV:

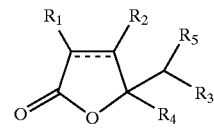

IV wherein $R_2$ is independently H, halogen, alkyl, alkoxy, oxoalkyl, alkenyl, aryl or arylalkyl whether unsubstituted or substituted, straight chain or branched chain, hydrophilic or fluorophilic;

$R_4$ is selected from halogen, OH and Oalkyl;

$R_5$ are halogen;

$R_1$ and $R_3$ are independently or both hydrogen or halogen;

and "====" is a single bond or double bond, to prepare a compound of formula V wherein $R_2$ is a H, alkyl, alkoxy, oxoalkyl, alkenyl, aryl or arylalkyl whether unsubstituted or substituted, straight chain or branched chain, hydrophobic, hydrophilic or fluorophilic;

$R_4$ is a halogen;

$R_1$ and $R_3$ are independently or both hydrogen or halogen;

the method comprising contacting a compound of formula IV with a base.

2. A method according to claim 1 wherein the base is selected from the group consisting of 1,4-diazabicyclo [2.2.2]octane (DABCO), 4-(dimethylamino)pyridine (DMAP), 1,8-diazabicyclo[5.4.0]undec-7-ene (DBU), triethylamine, alkali metal carbonate, alkali metal acetate and N,N'-diisopropylethyl amine (Hunig's base).

3. A method according to claim 1 wherein $R_1$ of formula (IV) is a halogen and the base is N,N-diisopropylethyl amine.

4. A method according to claim 1, wherein the compound of formula V is selected from the group consisting of a compounds 5a–m:

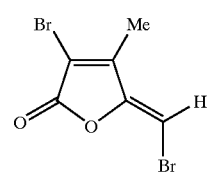

5a

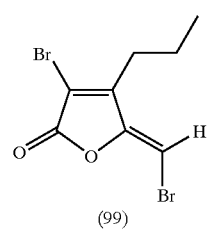

5b (99)

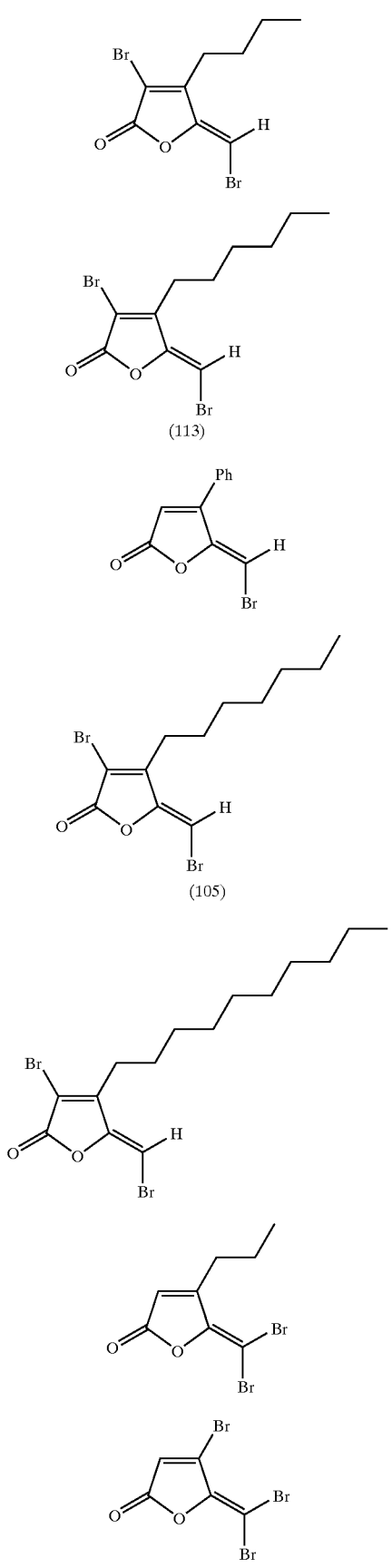

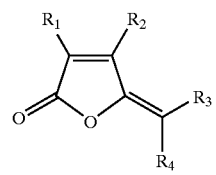

5. A compound of formula V:

$$V$$

wherein $R_2$ is an alkyl, alkoxy, oxoalkyl, alkenyl, aryl or arylalkyl whether unsubstituted or substituted, straight chain or branched chain, hydrophobic, hydrophilic or fluorophilic;

$R_4$ is a halogen;

$R_1$ and $R_3$ are independently or both hydrogen or halogen; excluding compounds in which: $R_1$=H, $R_2$=Me or Ph, $R_3$=I, $R_4$=H; and $R_1$=H, $R_2$=OMe, $R_3$=Cl, $R_4$=Cl.

6. An oligomer or polymer formed by oligomerising or polymerising a compound of formula V, directly or with one or more monomers

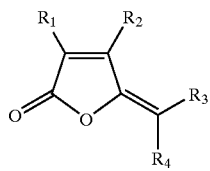

IIIa wherein $R_2$ is an alkyl, alkoxy, oxoalkyl, alkenyl, aryl or arylalkyl whether unsubstituted or substituted, straight chain or branched chain, hydrophobic, hydrophilic or fluorophilic;
$R_4$ is a halogen
$R_1$ and $R_3$ are independently or both hydrogen or halogen;

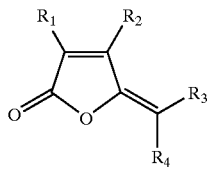

IIIb wherein $R_2$ is an alkyl, alkoxy, oxoalkyl, alkenyl, aryl or arylalkyl whether unsubstituted or substituted, straight chain or branched chain, hydrophobic, hydrophilic or fluorophilic;
$R_3$ and $R_4$ are hydrogen; and
$R_1$ is a halogen,

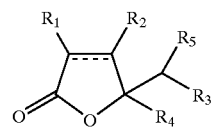

IV wherein $R_2$ is independently H, halogen, alkyl, alkoxy, oxoalkyl, alkenyl, aryl or arylalkyl whether unsubstituted or substituted, straight chain or branched chain, hydrophilic or fluorophilic;
$R_4$ is selected from halogen, OH and Oalkyl;
$R_5$ are halogen;
$R_1$ and $R_3$ are independently or both hydrogen or halogen; and "===" is a single bond or double bond,

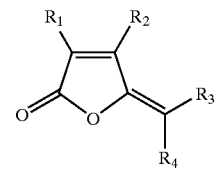

V wherein $R_2$ is a H, alkyl, alkoxy, oxoalkyl, alkenyl, aryl or arylalkyl whether unsubstituted or substituted, straight chain or branched chain, hydrophobic, hydrophilic or fluorophilic;
$R_4$ is a halogen;
$R_1$ and $R_3$ are independently or both hydrogen or halogen;

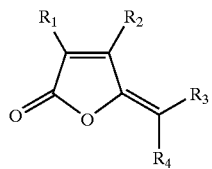

VI wherein $R_2$ is a H, halogen, alkyl, alkoxy, oxoalkyl, alkenyl, aryl or arylalkyl whether unsubstituted or substituted, straight chain or branched chain, hydrophobic, hydrophilic or fluorophilic;
$R_4$ is a halogen;
$R_1$ is hydrogen; and
$R_3$ is a hydrogen or halogen;

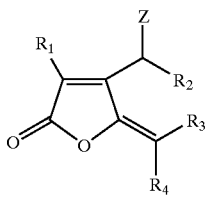

VII wherein $R_2$ is a H, alkyl, alkoxy, oxoalkyl, alkenyl, aryl or arylalkyl whether unsubstituted or substituted, straight chain or branched chain, hydrophobic, hydrophilic or fluorophilic;
$R_4$ is a hydrogen, halogen;
$R_1$ and $R_3$ are independently or both hydrogen or halogen;
z is independently selected from the group $R_2$, halogen, $OC(O)R_2$, =O, amine azide, thiol, $R_2$, mercaptoaryl, arylalkoxy, mercaptoarylalkyl, $SC(O)R_2$, $OS(O)_2R_2$, $NHC(O)R_2$, =$NR_2$ or $NHR_2$.

7. An oligomer or polymer according to claim 6, where the at least one monomer is selected from the group consisting of acrylate ester such as alkyl, hydroxyalkyl, aminoalkyl, or substituted aryl acrylates or methacrylates, crotonates, substituted or unsubstituted acrylonitriles, vinyl alcohols or acetates, styrene and siloxanes.

8. An article incorporating at least one compound of formula V in a surface coating(s) or polymer(s) through the newly introduced functionality on the alkyl chain or the alkyl chain itself via direct polymerisation or copolymerisation with suitable monomers.

* * * * *